(12) United States Patent
Repko et al.

(10) Patent No.: US 12,097,645 B2
(45) Date of Patent: Sep. 24, 2024

(54) AUTOMATION MECHANISM FOR PRE/CLINICAL PRODUCTION OF RESORBABLE NERVE GUIDES

(71) Applicant: UNIVERSITY OF PITTSBURGH—OF THE COMMONWEALTH SYSTEM OF HIGHER EDUCATION, Pittsburgh, PA (US)

(72) Inventors: Alexander James Repko, Pittsburgh, PA (US); Kacey Gribbin Marra, Canonsburg, PA (US); Benjamin Schilling, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 328 days.

(21) Appl. No.: 17/474,197

(22) Filed: Sep. 14, 2021

(65) Prior Publication Data

US 2021/0402654 A1     Dec. 30, 2021

Related U.S. Application Data

(63) Continuation of application No. PCT/US2020/023708, filed on Mar. 19, 2020.
(Continued)

(51) Int. Cl.
*B29C 41/14* (2006.01)
*B29C 41/22* (2006.01)
(Continued)

(52) U.S. Cl.
CPC .............. *B29C 41/14* (2013.01); *B29C 41/22* (2013.01); *B29C 41/52* (2013.01); *A61L 27/18* (2013.01);
(Continued)

(58) Field of Classification Search
CPC ..................................................... B29C 41/14
See application file for complete search history.

(56) References Cited

U.S. PATENT DOCUMENTS

| | | | |
|---|---|---|---|
| 2,090,528 A | | 8/1937 | Ferngren |
| 3,166,791 A | * | 1/1965 | Miller ..................... B29C 41/14 |
| | | | 425/173 |

(Continued)

OTHER PUBLICATIONS

International Search Report mailed Nov. 23, 2020 in International Application No. PCT/US20/23708.

*Primary Examiner* — Cachet I Proctor
(74) *Attorney, Agent, or Firm* — Baker Botts L.L.P.

(57) ABSTRACT

The presently disclosed subject matter relates to systems for making an implantable construct comprising a reservoir coupled to the at least one frame; a mandrel base coupled to the at least one frame; a mandrel coupled to the mandrel base; a first mechanism configured to be coupled to the at least one frame and configured to move the at least one frame along a first axis; a second mechanism configured to be coupled to the at least one frame and configured to rotate the least one mandrel base along a second axis between a first orientation and a second orientation; and a container configured to be coupled to the at least one frame and configured to receive the mandrel in the second orientation. The disclosed mechanisms can manually, semi-automatically, or automatically control the movements of the at least one frame, reservoir, mandrel, mandrel base, and container to produce the construct with a lumen. The presently dis- (Continued)

closed subject matter also relates to methods for making the construct.

14 Claims, 19 Drawing Sheets

Related U.S. Application Data

(60) Provisional application No. 62/820,425, filed on Mar. 19, 2019.

(51) Int. Cl.
  *B29C 41/52* (2006.01)
  *A61L 27/18* (2006.01)
  *B29L 31/00* (2006.01)

(52) U.S. Cl.
  CPC . *B29K 2995/006* (2013.01); *B29L 2031/7532* (2013.01)

(56) References Cited

U.S. PATENT DOCUMENTS

| | | | | |
|---|---|---|---|---|
| 4,863,668 | A * | 9/1989 | Griffiths | A61B 17/1128 264/307 |
| 4,867,983 | A * | 9/1989 | Berta | A61K 9/2873 118/30 |
| 7,534,464 | B2 * | 5/2009 | Kokish | A61F 2/82 427/372.2 |
| 7,780,897 | B2 | 8/2010 | Wicker et al. | |
| 8,366,770 | B2 | 2/2013 | Xu | |
| 2010/0178414 | A1 * | 7/2010 | Judge | B29C 41/06 427/2.24 |
| 2013/0189435 | A1 | 7/2013 | Mackie et al. | |
| 2014/0265061 | A1 * | 9/2014 | Hall | D01D 7/00 425/402 |
| 2018/0112167 | A1 | 4/2018 | Kang et al. | |

* cited by examiner

AUTOMATION MECHANISM FOR PRE/CLINICAL PRODUCTION OF RESORBABLE NERVE GUIDES

1. PRIORITY CLAIM

This application is a continuation of International Patent Application No. PCT/US2020/023708 filed Mar. 19, 2020, which claims priority to U.S. Provisional Application Ser. No. 62/820,425 filed Mar. 19, 2019, the contents of which are hereby incorporated by reference in their entireties.

2. GRANT INFORMATION

This invention was made with government support under grant W81XWH-14-2-0003 awarded by the U.S. Army Medical Research and Materiel Command (ARMY/MRMC), and grant DE026915 awarded by the National Institutes of Health (NIH). The government has certain rights in the invention.

3. BACKGROUND

Extremity and nerve-related injuries can be common injuries sustained in a battlefield. Particularly challenging is the repair of long gap peripheral nerve injuries (e.g., defects>3 cm). Certain treatments (e.g., autograft) can be applied for such injuries. However, existing treatments have certain limitations. For example, autografting requires harvesting and transferring a patient's own nerve. The use of the autograft requires a second surgical site resulting in longer operating times. Furthermore, when a sensory nerve is used to replace a motor/sensory nerve, it can cause permanent numbness in a certain area of a body. If autografting cannot be performed due to a lack of donor tissue, an alternative for injury repair can be a decellularized allograft nerve guide. Commercially available allografts, however, cannot offer the same cellular cues relative to autograft, where the Schwann cell secretome can be essential for nerve regrowth, resulting in suboptimal repair.

Accordingly, there remains a need for systems and techniques for producing biodegradable constructs that can address the above-mentioned limitations.

4. SUMMARY

One embodiment of the presently disclosed subject matter provides a system for making a construct comprising a reservoir coupled to the at least one frame; a mandrel base coupled to the at least one frame; a mandrel coupled to the mandrel base; a first mechanism configured to be coupled to the at least one frame and configured to move the at least one frame along a first axis; a second mechanism configured to be coupled to the at least one frame and configured to rotate the least one mandrel base along a second axis between a first orientation and a second orientation; and a container configured to be coupled to the at least one frame and configured to receive the mandrel in the second orientation.

In certain embodiments, the produced construct can comprise a tube having a lumen. The tube can include an inner layer and an outer layer, wherein the inner layer can be selected from the group consisting of a first biodegradable polymer, a particle, an active agent and combinations thereof, wherein the outer layer can be selected from the group consisting of a second biodegradable polymer, the particle, the active agent, and combinations thereof. In non-limiting embodiments, the particle can be selected from the group consisting of a microsphere, a nanosphere, and a combination thereof. For example, the at least one particle can include a double-walled particle, wherein the double-walled particle can include the active agent that can be released over a pre-determined period of time.

In certain embodiments, the mandrel can be selected from the group consisting of a biodegradable structure, a biologically-derived structure, a bioactive structure, and combinations thereof. For example, the mandrel can include or comprise a cylindrical structure of purified collagen or a decellularized scaffold.

In certain embodiments, the first mechanism can be configured to be coupled to the at least one frame and move the at least one frame along a first axis. The first axis can be a vertical axis. The first mechanism can change a location of the at least one mandrel from a first position at least in part within the reservoir to a second position outside the reservoir, or vice versa.

In certain embodiments, the second mechanism can be configured to be coupled to the at least one frame and rotate the least one mandrel base along a second axis from a first orientation to a second orientation. The second axis can be a horizontal axis. The first orientation can be a vertical orientation, and the second orientation can be a horizontal orientation.

In certain embodiments, the container can be configured to be coupled with the at least one frame and receive the mandrel in the second orientation. The container can include a particle, wherein the particle can be selected from the group consisting of a microsphere, a nanosphere, and a combination thereof.

In certain embodiments, the disclosed system can further comprise a third mechanism configured to move the first container from a first position away from the mandrel in the second orientation to a second position to receive the mandrel in the second orientation.

In certain embodiments, the reservoir can be configured to be coupled to the at least one frame. The reservoir can comprise a polymer solution. For example, the reservoir can include a polycaprolactone (PCL) solution.

In certain embodiments, the disclosed system can further comprise a housing. The disclosed system can be located in a housing that can monitor and control temperature and humidity within the housing.

In certain embodiments, the disclosed system can further comprise a microcontroller, wherein the mechanisms are manually, semi-automatically, or automatically controlled by the microcontroller. In non-limiting embodiments, the microcontroller can monitor, record, and save data related to conditions of the disclosed system. The conditions can include temperature and humidity.

In certain embodiments, the disclosed system can include two or more mandrel bases and reservoirs, wherein the mechanisms control movement of the two or more mandrel bases together or independently.

Another embodiment of the present application provides a method of making a construct comprising dipping a mandrel in a first polymer solution to produce a coated mandrel, wherein the mandrel is in a first orientation; removing the coated mandrel from the first polymer solution; rotating the coated mandrel to a second orientation different from the first orientation, contacting the coated mandrel with a particle to produce a particle embedded mandrel, wherein the particle embedded mandrel comprises a first polymer layer which includes at least a portion of the particle; rotating the particle embedded mandrel to, or substantially to the first orientation; dipping the particle embedded mandrel in a second polymer solution to deposit a second polymer layer over the particle; and removing the particle embedded mandrel with the second polymer layer from the second polymer solution.

In certain embodiments, the second orientation can be perpendicular or substantially perpendicular to the first orientation.

In certain embodiments, the disclosed method can further include repeating the dipping and removing the particle embedded mandrel from the second polymer solution; and drying the particle embedded mandrel between each dipping of the mandrel in the second polymer solution.

In certain embodiments, the disclosed method can further include contacting the particle-embedded mandrel with the second polymer layer with an additional particle. In certain embodiments, the disclosed method can further include dipping and removing the coated mandrel from an additional polymer solution before contacting with the particle.

5. BRIEF DESCRIPTION OF THE FIGURES

Figure 7A:
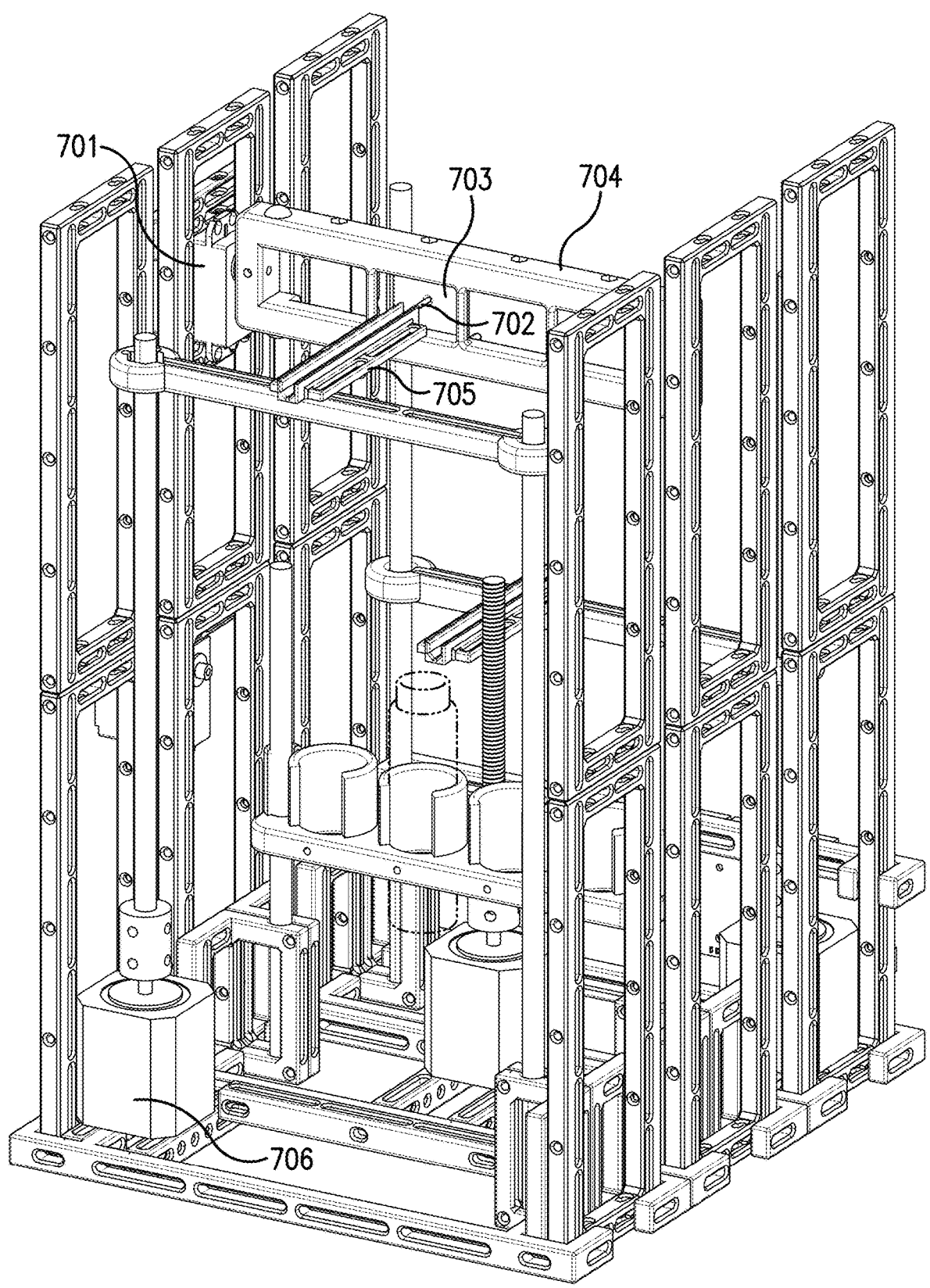
Figure 7B:
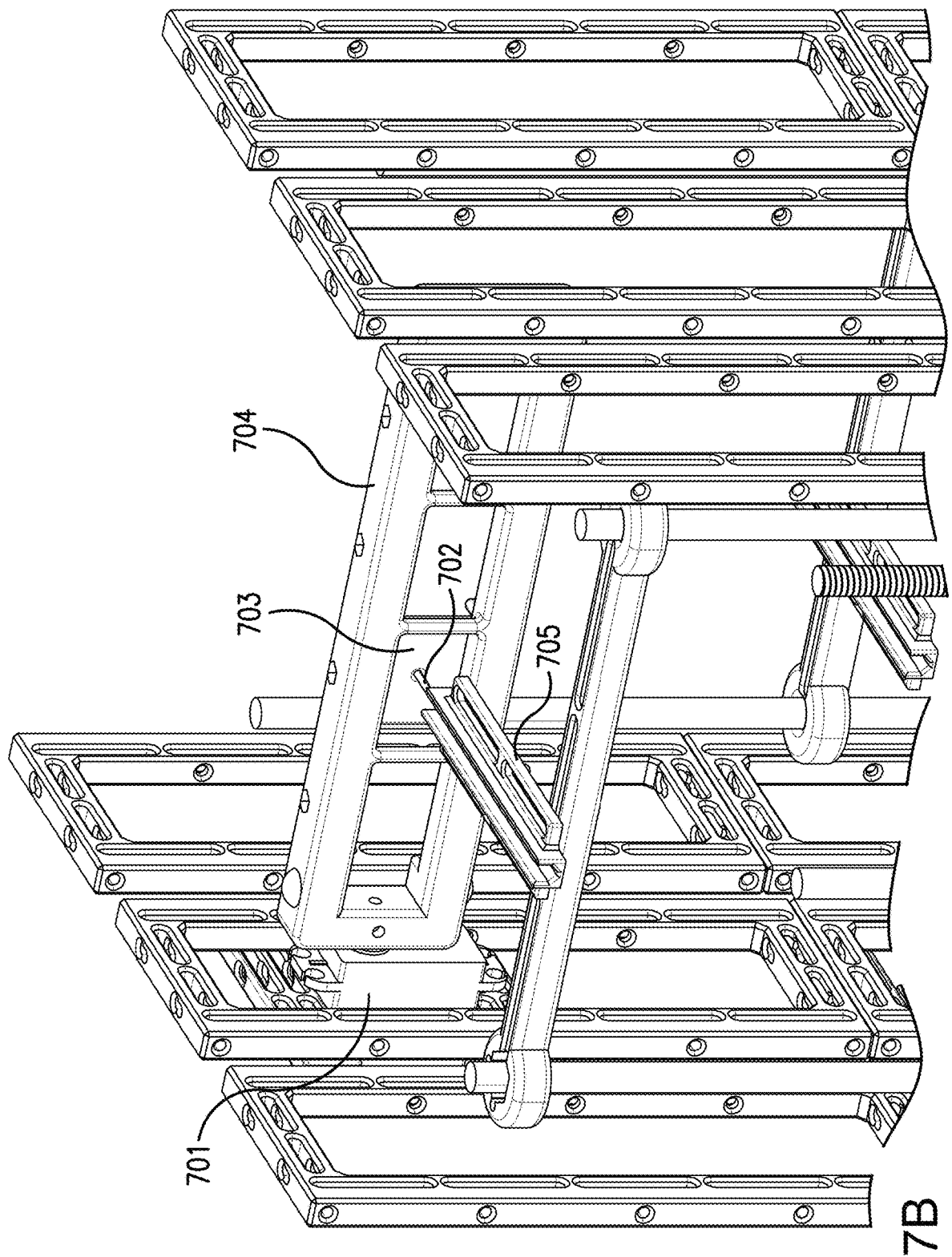

FIG. 7A is an exemplary schematic of the disclosed system at the position where a mandrel is oriented to 90 degrees in accordance with certain non-limiting embodiments of the disclosed subject matter. FIG. 7B is an exemplary magnified schematic of the disclosed system at the position where a mandrel is oriented to 90 degrees in accordance with certain non-limiting embodiments of the disclosed subject matter.

Figure 8A:
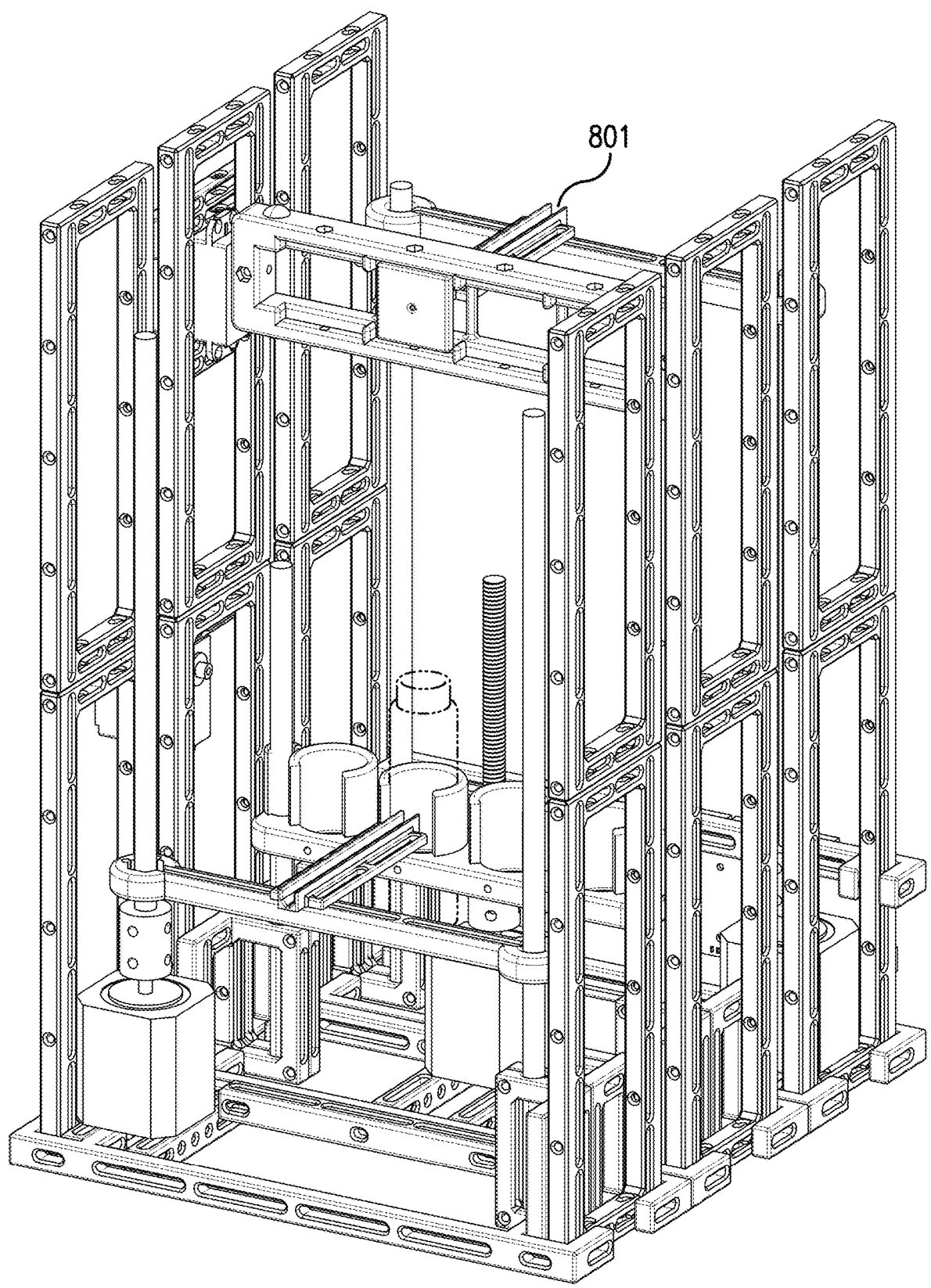
Figure 8B:
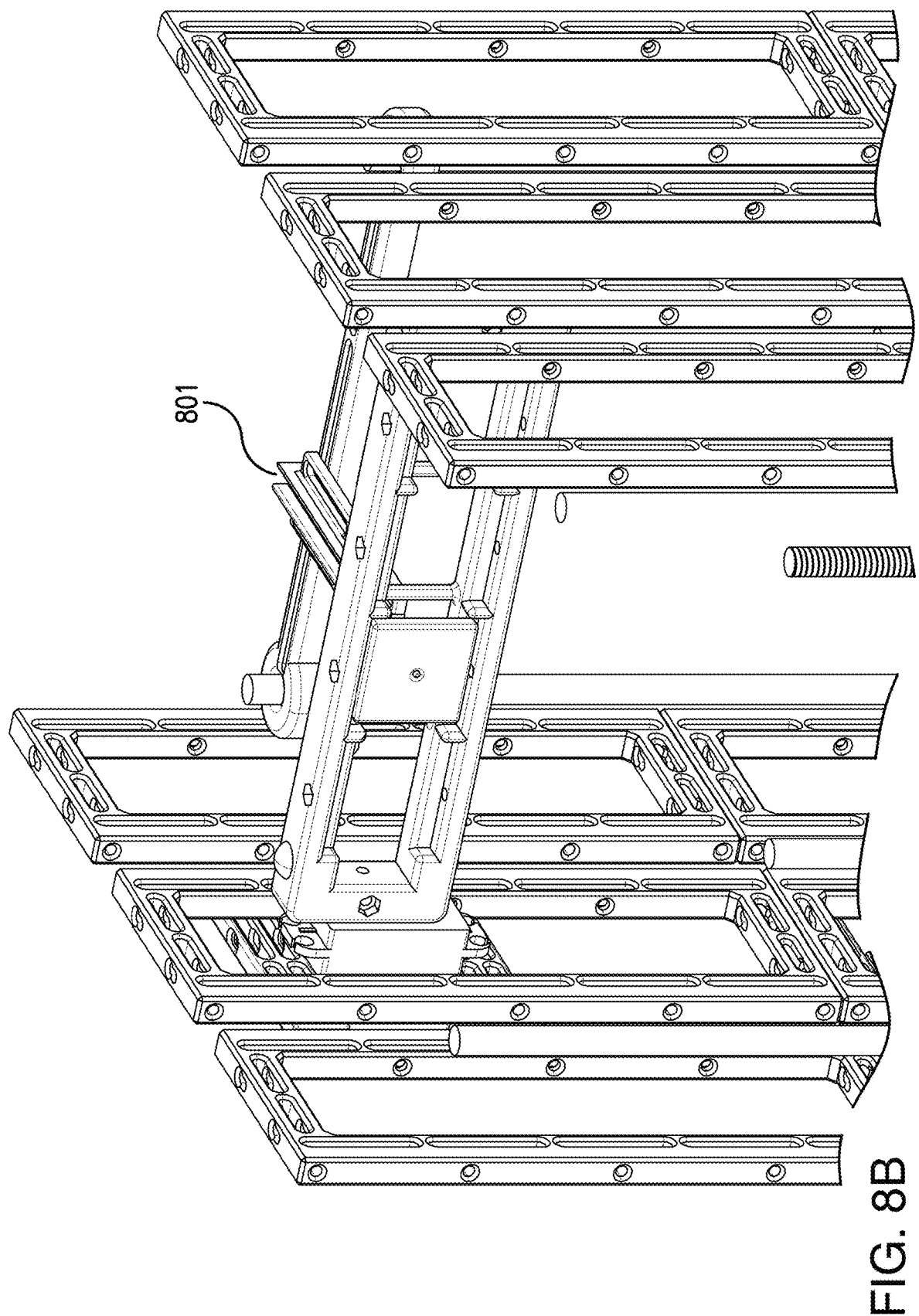

FIG. 8A is an exemplary schematic of the disclosed system at the position where a mandrel is oriented to 270 degrees in accordance with certain non-limiting embodiments of the disclosed subject matter. FIG. 8B is an exemplary magnified schematic of the disclosed system at the position where a mandrel is oriented to 270 degrees in accordance with certain non-limiting embodiments of the disclosed subject matter.

Figure 9:
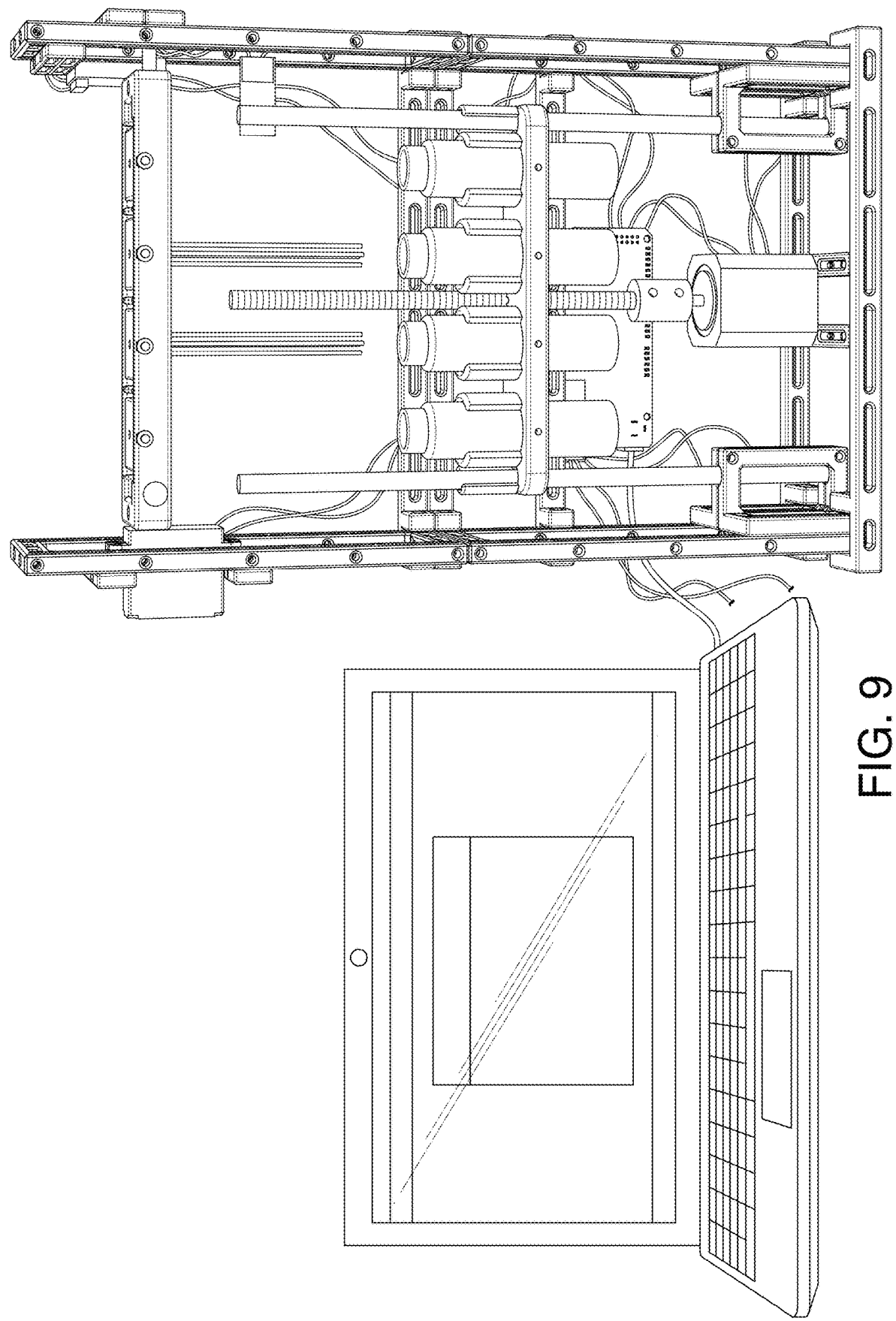

FIG. 9 is an exemplary photograph of the automated system in accordance with certain non-limiting embodiments of the disclosed subject matter.

Figure 10:
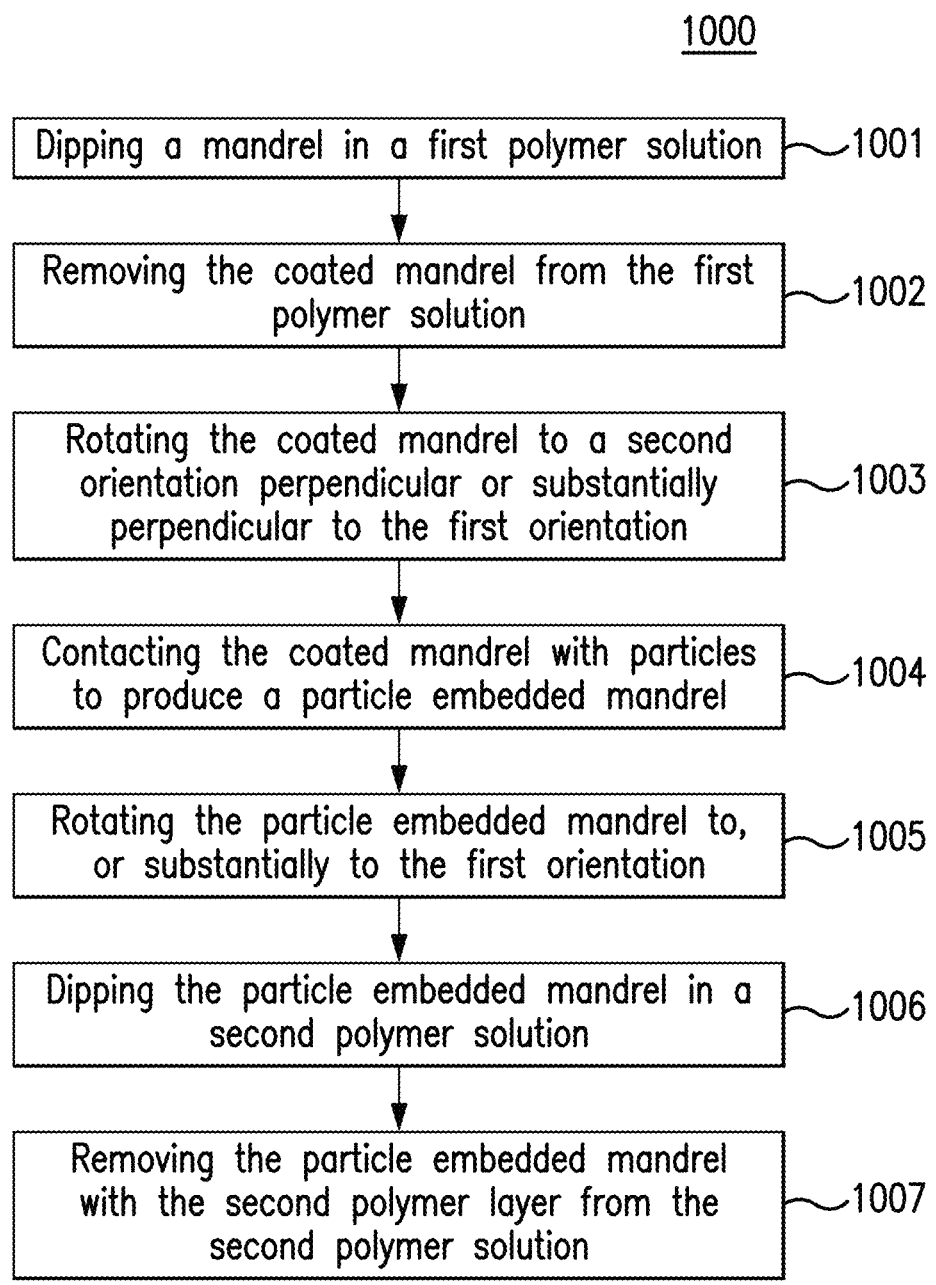

FIG. 10 provides an exemplary method for making a construct in accordance with certain non-limiting embodiments of the disclosed subject matter.

Figure 11B:
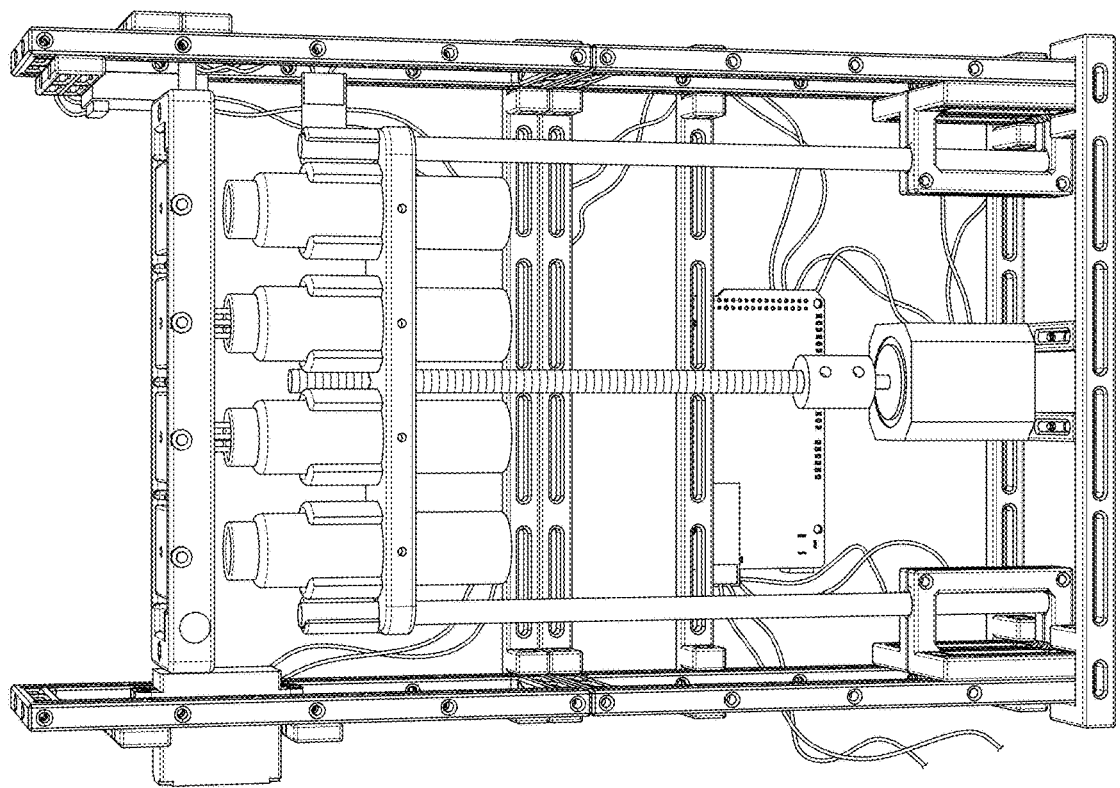
Figure 11A:
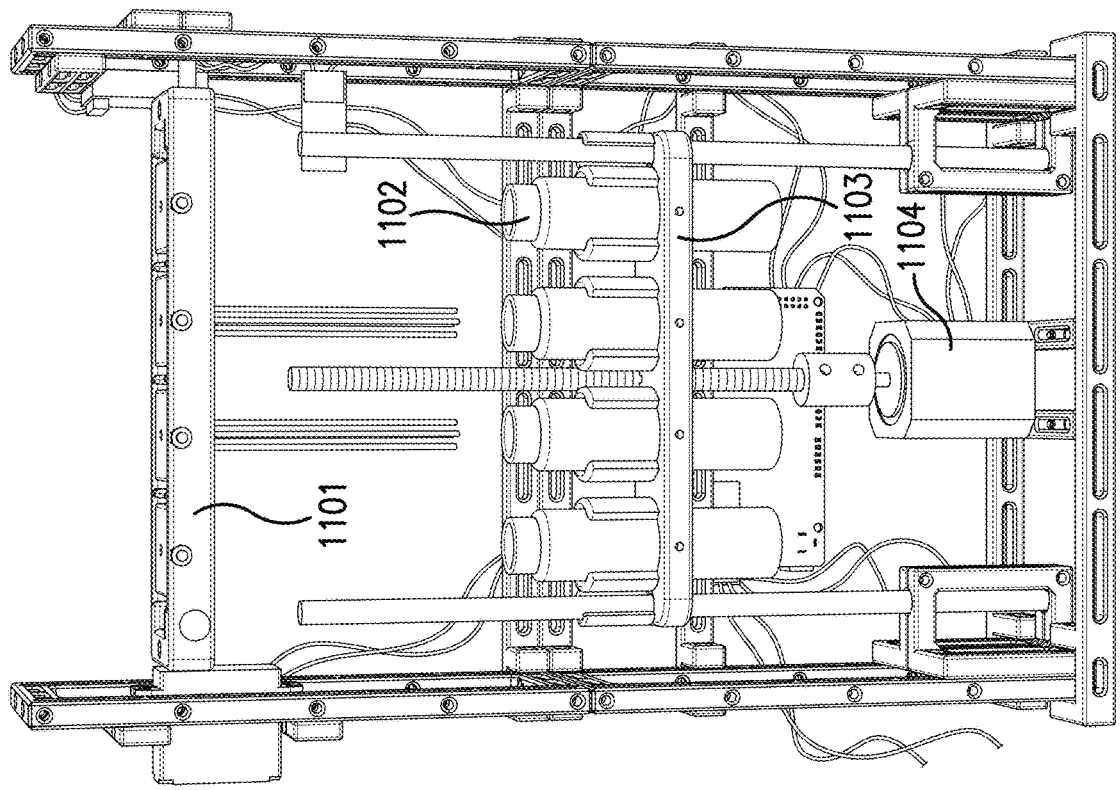
Figure 11D:
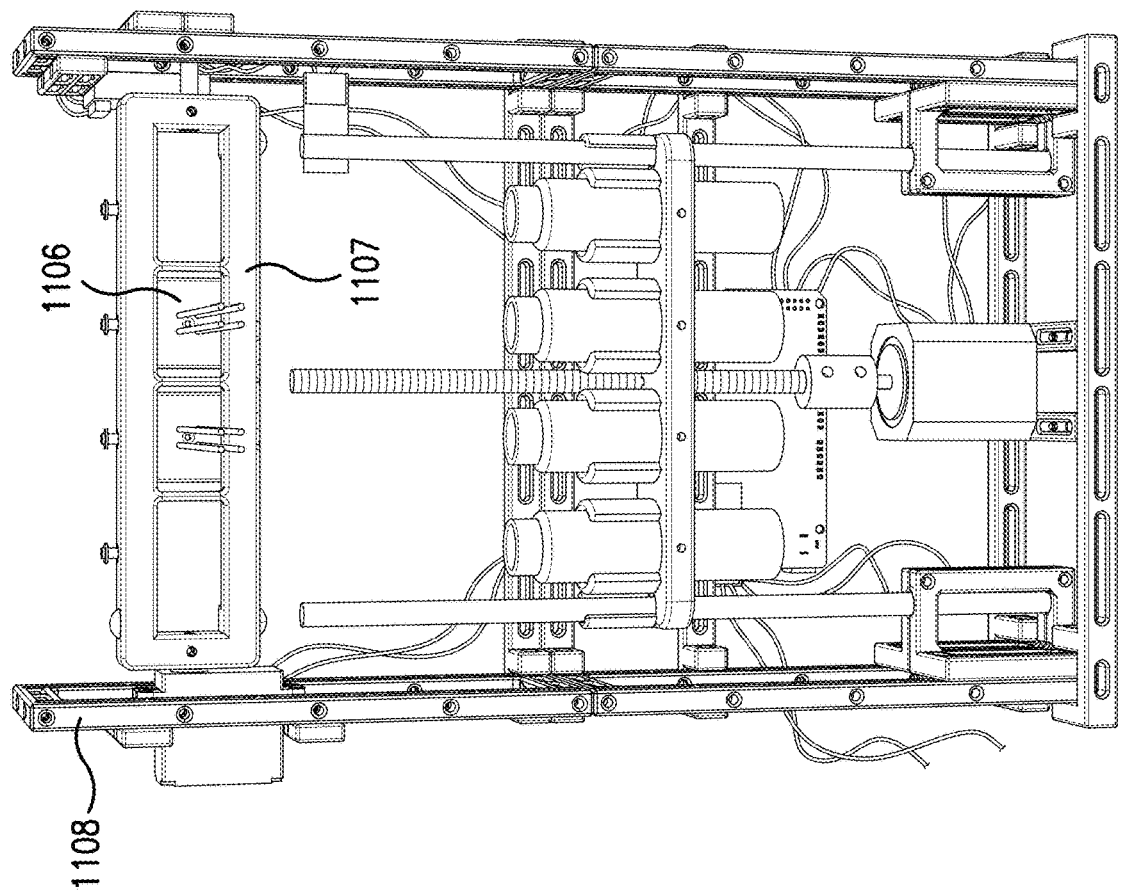
Figure 11C:
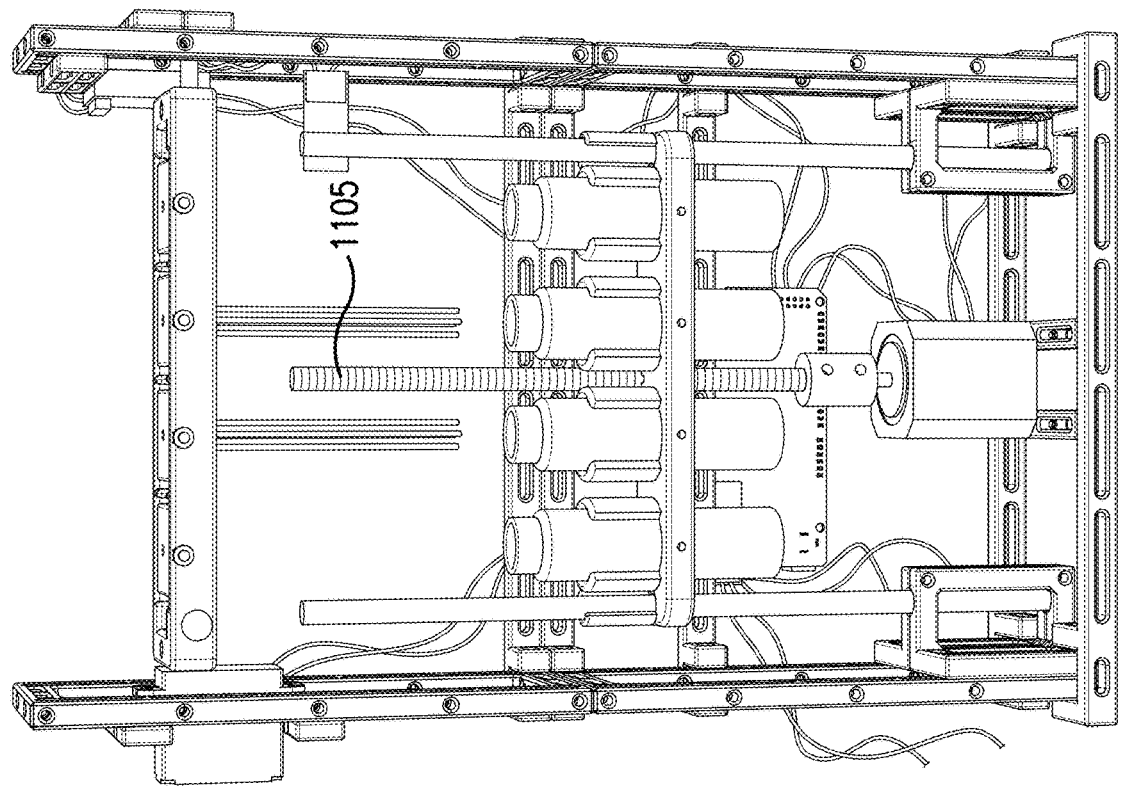
Figure 11F:
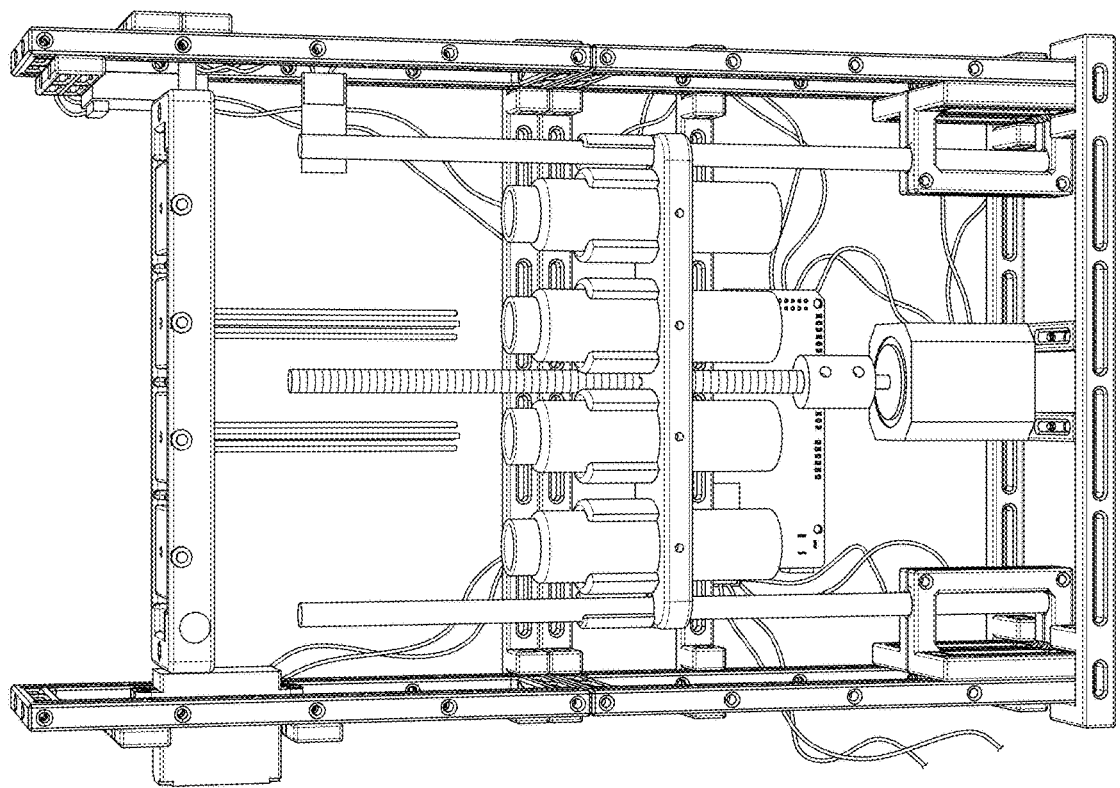
Figure 11E:
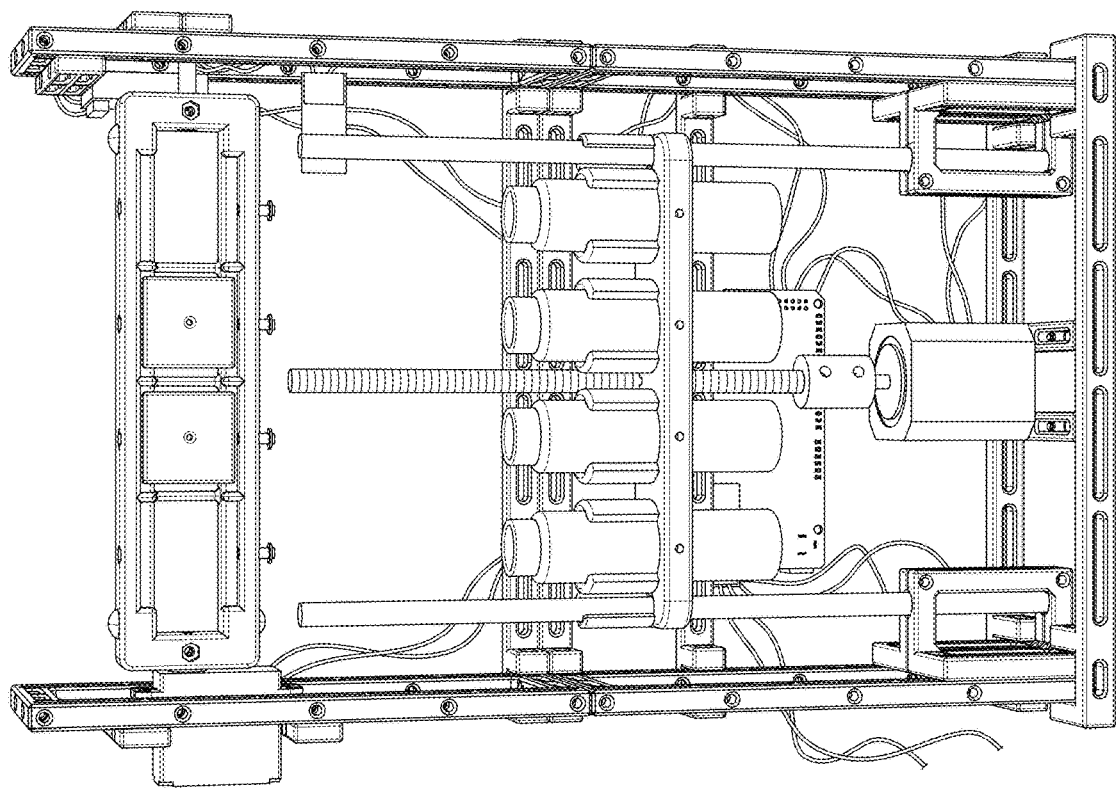
Figure 11H:
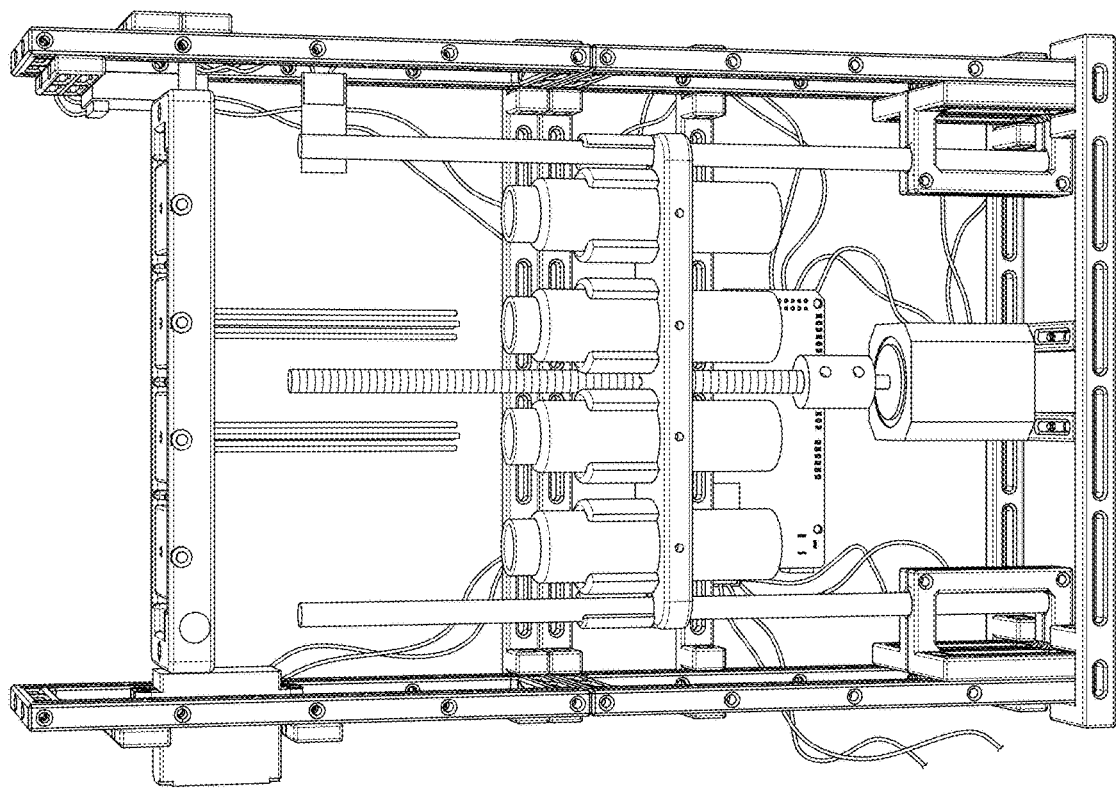
Figure 11G:
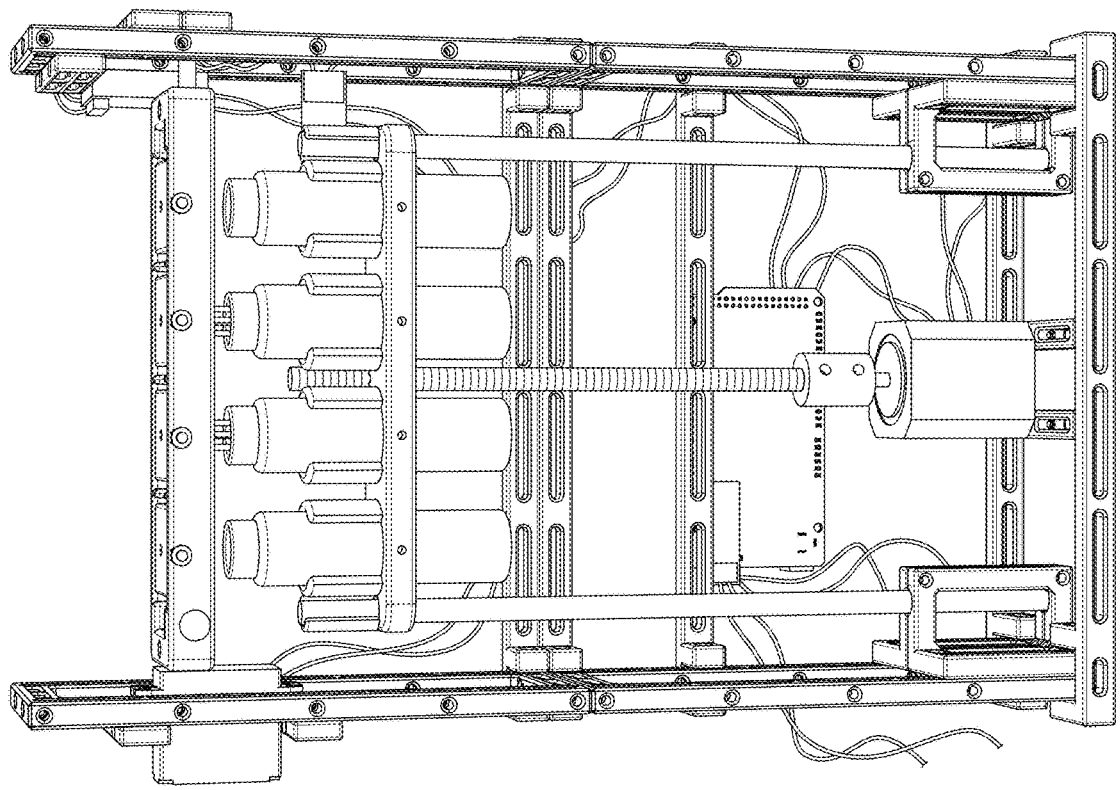

FIG. 11A-H provides exemplary photographs showing the automated movements of the disclosed system in accordance with certain non-limiting embodiments of the disclosed subject matter. FIG. 11A is a photograph showing an exemplary automated system including the reservoir, two mandrel bases, four mandrels, the microcontroller, the first mechanism, and the second mechanism. FIG. 11B is a photograph showing that the microcontroller controls the movements of frames using the first mechanism to dip the mandrels into a PCL solution in the reservoir. FIG. 11C is a photograph showing that the microcontroller controls the movements of frames using the first mechanism to move the mandrels outside of the reservoir. FIG. 11D is a photograph showing that the mandrel bases with mandrels are rotated 90 degrees by the second mechanism. FIG. 11E is a photograph showing that the mandrel bases with mandrels are rotated 270 degrees by the second mechanism. FIG. 11F is a photograph showing that the mandrel bases with mandrels are oriented back to the 0-degree position for additional dipping process. FIG. 11G is a photograph showing that the mandrels are dipped into the reservoir for the additional dipping process. FIG. 11H is a photograph showing that the mandrels are moved outside of the reservoir for further process.

Figure 12B:
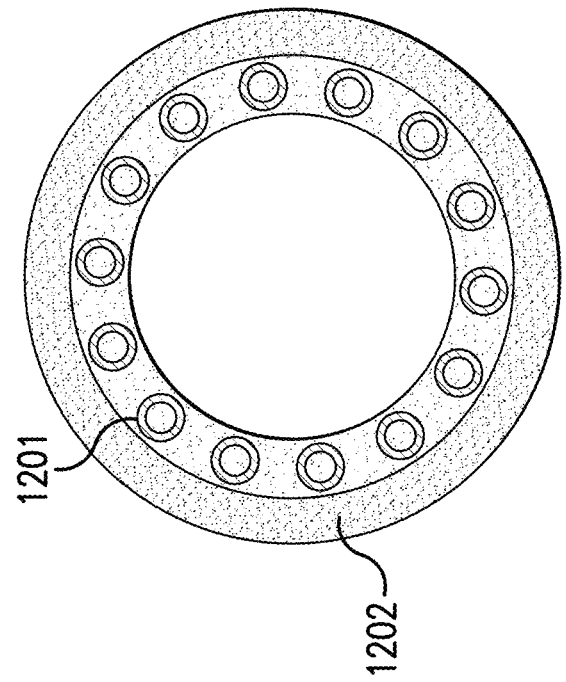
Figure 12A:
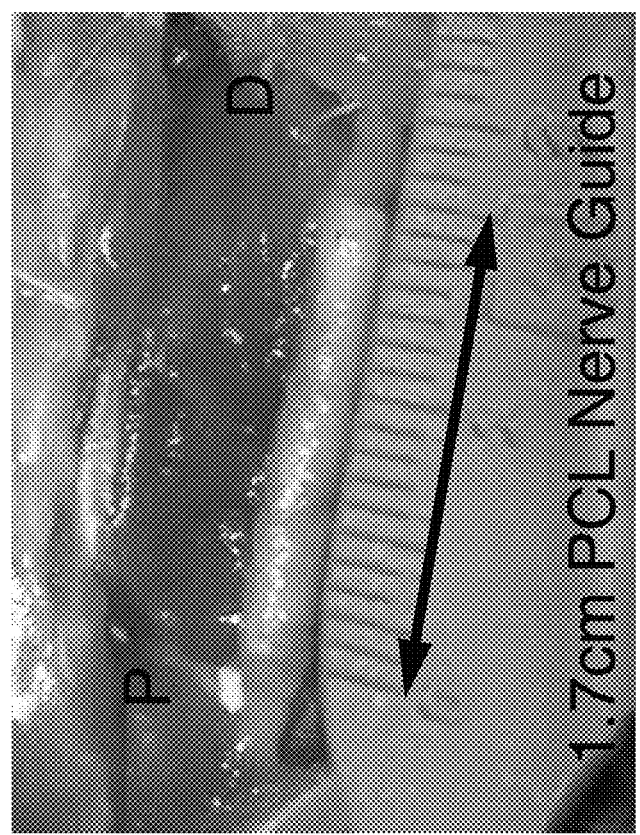

FIG. 12A is an exemplary photograph of the construct in accordance with certain non-limiting embodiments of the disclosed subject matter. FIG. 12B is a schematic of a cross-section view of the construct in accordance with certain non-limiting embodiments of the disclosed subject matter.

6. DETAILED DESCRIPTION

The presently disclosed subject matter relates to systems for making an implantable construct comprising at least one frame, a reservoir, a mandrel, a mandrel base, a first mechanism, a second mechanism, and a container. The disclosed mechanisms can manually, semi-automatically, or automatically control the movements of the at least one frame, reservoir, mandrel, mandrel base, and container to produce the construct with a lumen. The presently disclosed subject matter also relates to methods for making the construct.

For clarity of description, and not by way of limitation, the detailed description of the disclosed subject matter is divided into the following subsections:

6.1 Definitions;
   6.2 Systems for making a construct;
   6.3 Methods of making a construct;
   6.4 Implantable construct; and
   6.5 Methods of promoting tissue regeneration.

6.1 Definitions

The terms used in this specification generally have their ordinary meanings in the art, within the context of the disclosed subject matter and in the specific context where each term is used. Certain terms are discussed below, or elsewhere in the specification, to provide additional guidance to the practitioner in describing the systems and methods of the disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open-ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "allograft" refers to a tissue graft from a donor of the same species as the recipient but genetically identical. For example, but not by limitation, the allograft tissue can include bone, bone marrow, kidney, liver, lung, corneal, pancreas, intestine, blood, uterus, thymus, ovary, tendons, ligaments, skin and heart valves.

The term "biomaterial" refers to a material that has properties that are adequate for mammalian body reconstruction, medical device construction, and/or drug control/release devices or products. This term includes absorbable devices and products, absorbable fabrics or meshes, absorbable adhesives, and absorbable drug control/release devices) as well as non-absorbable devices and products, (e.g., implantable repair, contact lens, or support meshes). The term "absorbable" as used herein refers to materials that will be degraded and subsequently absorbed by the body. The term "non-absorbable" as used herein refers to materials that will not be degraded and subsequently absorbed by the body.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of," and "consisting essentially of," the embodiments or elements presented herein, whether explicitly set forth or not.

The term "decellularized organ" as used herein refers to an organ or part of an organ from which the entire cellular and tissue content has been removed, leaving behind a complex interstitial structure. Organs are composed of various specialized tissues. The specialized tissue structures of an organ are the parenchyma tissue, and they provide the specific function associated with the organ. Most organs also have a framework composed of unspecialized connective tissue that supports the parenchyma tissue. The process of decellularization removes the parenchyma tissue, leaving behind the three-dimensional interstitial structure of connective tissue, primarily composed of collagen. The interstitial structure has the same shape and size as the native organ, providing the supportive framework that allows cells to attach to and grow on it. Decellularized organs can be rigid, or semi-rigid, having an ability to alter their shapes. Examples of decellularized organs include, but are not limited to, the heart, nerve, kidney, liver, pancreas, spleen, bladder, ureter, and urethra.

As used herein, the term effective amount refers to that amount of active agent (e.g., Glial Cell Line-Derived Neurotrophic Factor (GDNF)) sufficient to treat, prevent, or manage a disease. Further, a therapeutically effective amount can mean the amount of active agent alone, or in combination with other therapies, that provides a therapeutic benefit in the treatment or management of the disease, which can include a decrease in severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

As used herein, a "mandrel" can refer to a shaped object that can be inserted into a certain workpiece. For example, the mandrel can comprise glass, metal, a polymer, a biocompatible component, a biological or biologically-derived component, or combinations thereof. The mandrel can be adapted to press-fit into a workpiece, or fixed by some other means into the workpiece.

As used herein, a "mechanism" refers to a device that transforms input forces and/or movements into a desired set of output forces and movements. For example, the mechanism can include a motor, a cylinder, a generator, a transformer, a turbine, a piston, or combinations thereof.

As used herein, a "protein" or "polypeptide" refers to a molecule comprising at least one amino acid residue.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. Ranges disclosed herein, for example, "between about X and about Y" are, unless specified otherwise, inclusive of range limits about X and about Y as well as X and Y. With respect to sub-ranges, "nested sub-ranges" that extend from either endpoint of the range are specifically contemplated. For example, a nested sub-range of an exemplary range of 1 to 50 can include 1 to 10, 1 to 20, 1 to 30, and 1 to 40 in one direction, or 50 to 40, 50 to 30, 50 to 20, and 50 to 10 in the other direction. Ranges disclosed herein, for example, "between about X and about Y" are, unless specified otherwise, inclusive of range limits about X and about Y as well as X and Y.

A "subject" herein may be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc. The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

6.2 Systems for Making a Construct

The disclosed subject matter provides systems for making a construct, which can be an implantable medical biomaterial and offer various cellular cues for tissue regeneration.

Figure 1:
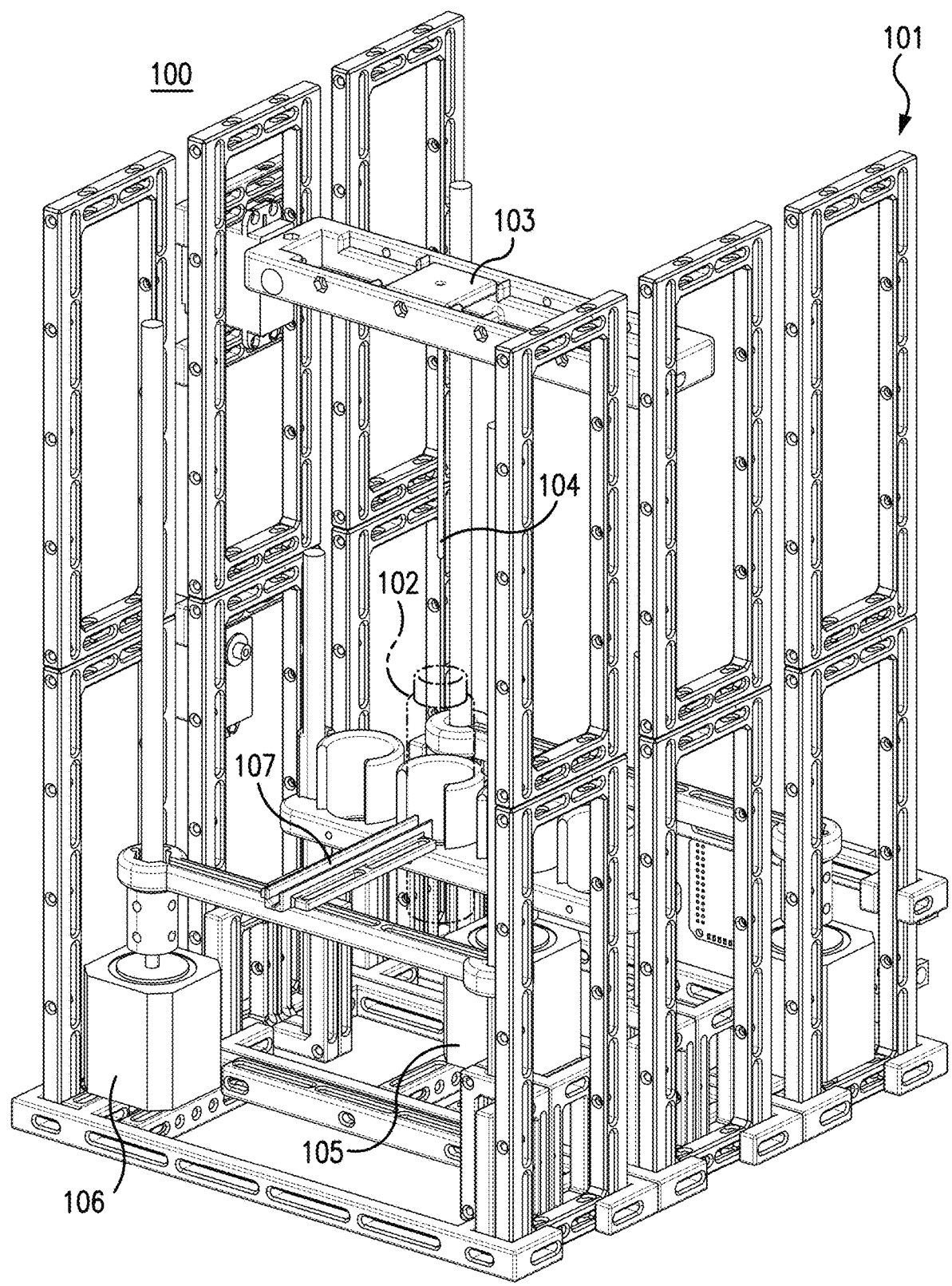
FIG. 1 is an exemplary schematic of the disclosed system in accordance with certain non-limiting embodiments of the disclosed subject matter.

In certain embodiments, the disclosed subject matter provides a system 100 for making a construct comprising at least one frame 101; a reservoir 102; a mandrel 103 base adapted to be coupled to the at least one frame 101; a mandrel 104; a first mechanism 105 configured to move the at least one frame 101, mandrel base 103, the reservoir 102, or combinations thereof along a first axis; a second mechanism 106 configured to rotate the mandrel base along a second axis a first orientation to a second orientation; and a container 107 configured to receive the mandrel in the second orientation (FIG. 1).

In certain embodiments, the disclosed system can include at least one frame. The frame can be attached or coupled to other components of the disclosed system (e.g., frame, reservoir, mandrel base, mechanism, container, etc.). The frame can be a structure that supports loads coming from the other components of the disclosed system. In non-limiting embodiments, the frame can comprise glass, metal, plastic, or combinations thereof. For example, the frame can include acrylonitrile butadiene styrene (ABS). In some embodiments, the frame can be produced using a three-dimensional (3D) printer. For example, the at least one frame can be designed using the Solid Works CAD/CAM software and printed using a fast filament fusion printer (FFF).

Figure 2:
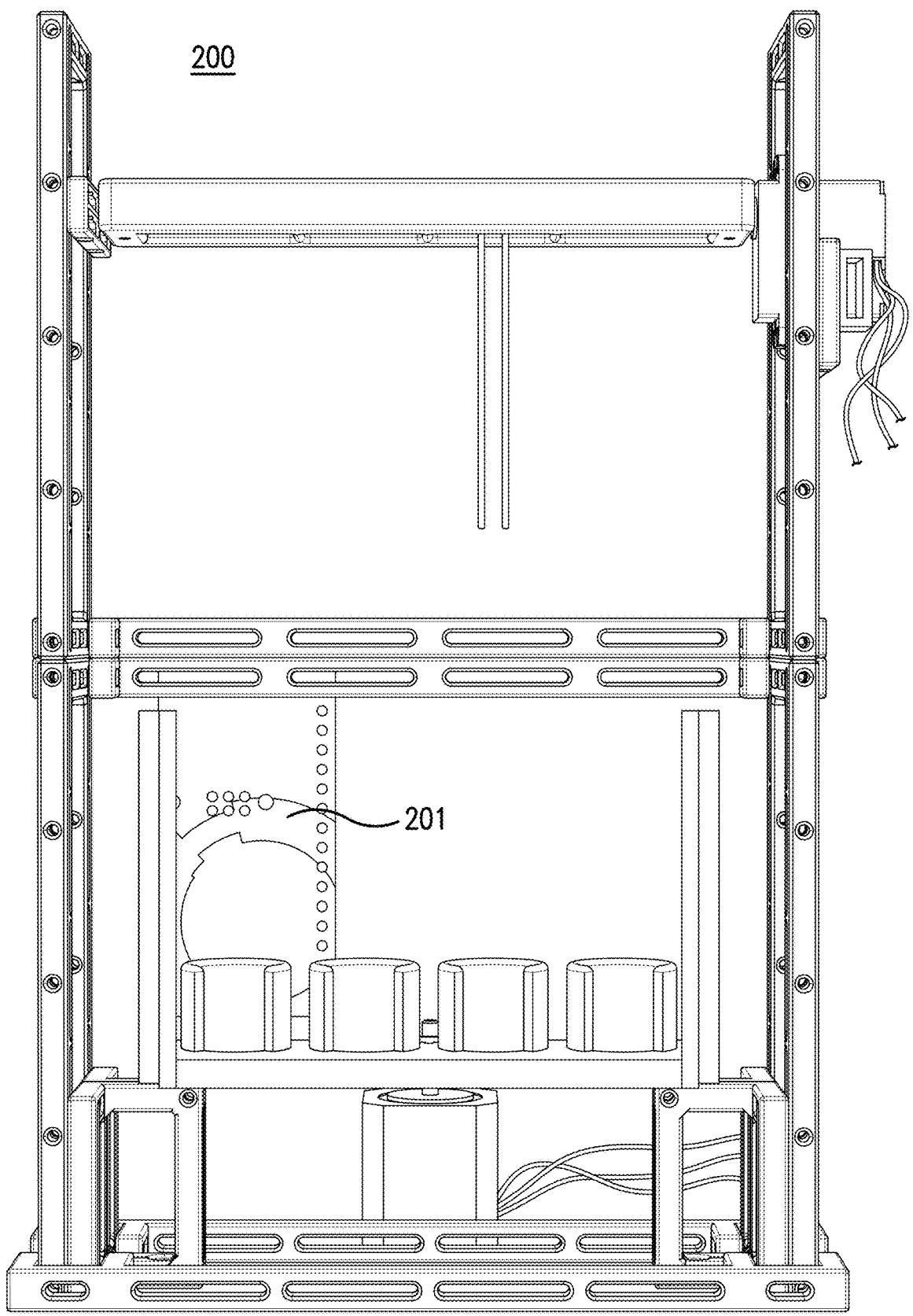
FIG. 2 is an exemplary photograph of frames in accordance with certain non-limiting embodiments of the disclosed subject matter.

In certain embodiments, the frame can freely move in all directions. For example, the frame can move along a vertical axis, a horizontal axis, or a diagonal axis. The frame can also be rotated and change its orientation. In non-limiting embodiments, a movement of the disclosed frame can be controlled by a microcontroller. For example, as shown in FIG. 2, all components of the disclosed system 200 can be electrically integrated via a printed circuit board (PCB) 201. The microcontroller can include automation software, which can be programmed in any suitable coding languages that allow communications with the PCB. For example, and not by way of limitation, the coding languages can include JavaScript, Python, Structured Query Language, PUP, Ruby, C, C++, C Sharp, Visual Basic, Java, Objective-C, Perl, LabVIEW, and other programming languages. In non-limiting embodiments, the microcontroller can monitor, record, and save data related to conditions of the disclosed system. For example, and not by way of limitation, the conditions of the disclosed system can include temperature and/or humidity.

Figure 3:
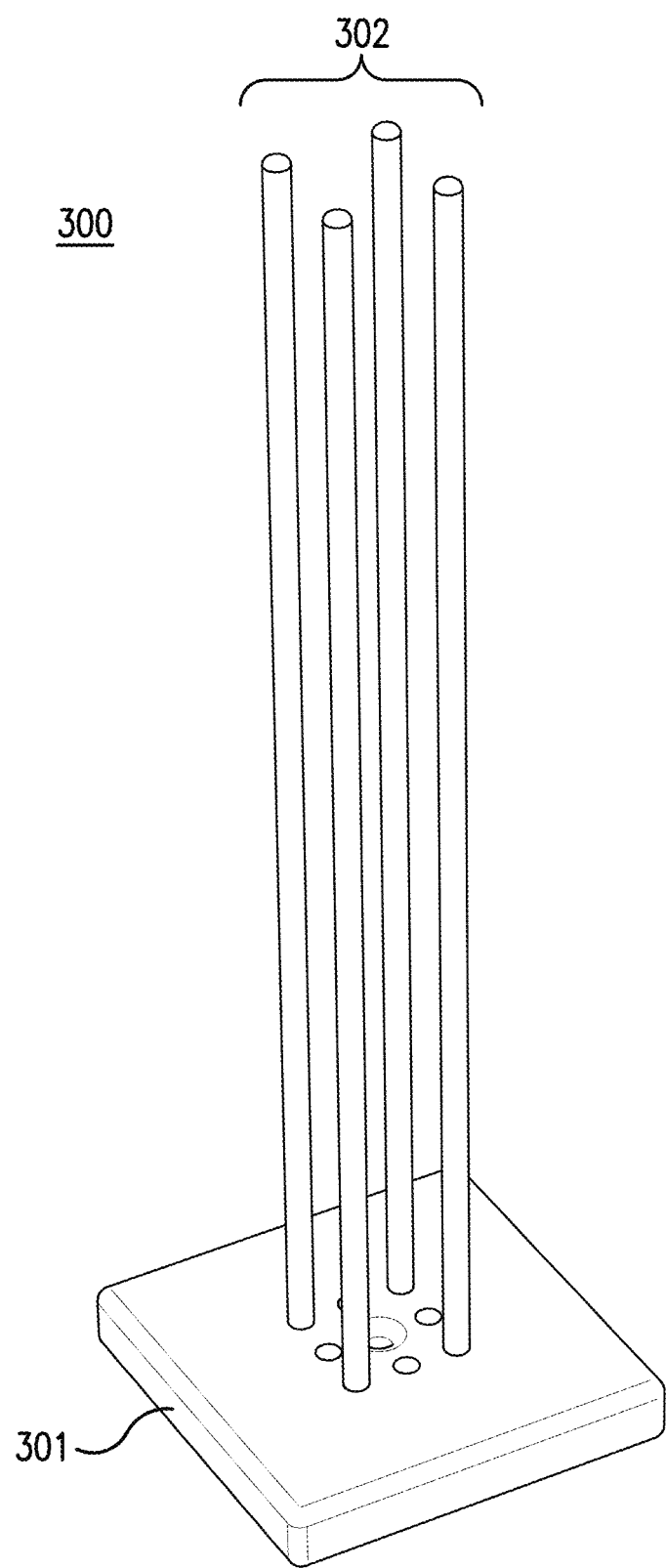
FIG. 3 is an exemplary photograph of a mandrel base with four mandrels in accordance with certain non-limiting embodiments of the disclosed subject matter.

In certain embodiments, the disclosed system includes a mandrel base 301 (FIG. 3). The mandrel base 301 can comprise glass, metal, plastic, or combinations thereof. For example, the mandrel base can include ABS. In non-limiting embodiments, the mandrel base can be produced using a 3D printer. In certain embodiments, the mandrel base can be configured to be coupled to at least one mandrel. For example, the mandrel base 301 can include at least one, at least two, at least three, at least four, at least five, at least six, at least seven, at least eight, at least nine, or at least ten holes where at least one mandrel can press-fit into (FIG. 3). In certain embodiments, the disclosed mandrel base can be attached or coupled to at least one frame of the disclosed system. For example, the disclosed mandrel base 401 can be mounted onto a mandrel base holder 401, which can be a part of the disclosed frame (FIGS. 4A and 4B).

In certain embodiments, the disclosed system can include a mandrel base holder 402. The mandrel base 402 can comprise glass, metal, plastic, or combinations thereof. For example, the mandrel base holder can include ABS. In non-limiting embodiments, the mandrel base holder can be produced using a 3D printer. In certain embodiments, the mandrel base holder can be configured to be coupled to at least one mandrel base. For example, the mandrel base holder 402 can include at least one, at least two, at least three, at least four (as shown, FIGS. 4A and 4B), at least five, at least six, at least seven, at least eight, at least nine, or at least ten locations where at least one mandrel base can be affixed. In certain embodiments, the mandrel base holder is capable of movement on a vertical, horizontal, diagonal, or rotational axis, or combinations thereof. In non-limiting embodiments, the disclosed system includes more than two mandrel bases.

In certain embodiments, the mandrel 302 can comprise glass, metal, a polymer, a biocompatible component, or combinations thereof (FIG. 3). The mandrel can be a structural base to create a construct with a lumen (e.g., tube shape). The disclosed mandrel can be removed from the construct after the creation of the construct prior to implantation. In non-limiting embodiments, the disclosed mandrel can include a biologically-derived structure, a bioactive structure, a biodegradable structure, or combinations thereof. For example, the mandrel can include a cylindrical geometry of purified collagen and/or a decellularized scaffold. In non-limiting embodiments, the disclosed system can create a construct where the mandrel is not removed from the construct but rather can be implanted as a combination. In some embodiments, at least one mandrel can be coupled to the disclosed mandrel base and then coated with polyvinyl acetate (PVA).

Figure 4B:
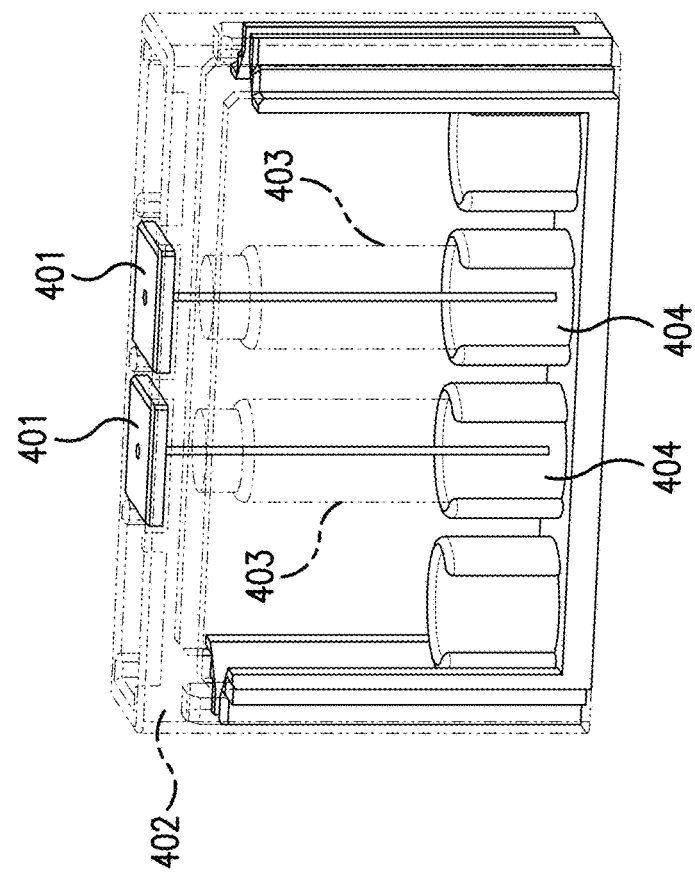
FIG. 4B is an exemplary schematic of a translucent dipping system in accordance with certain non-limiting embodiments of the disclosed subject matter.
Figure 4A:
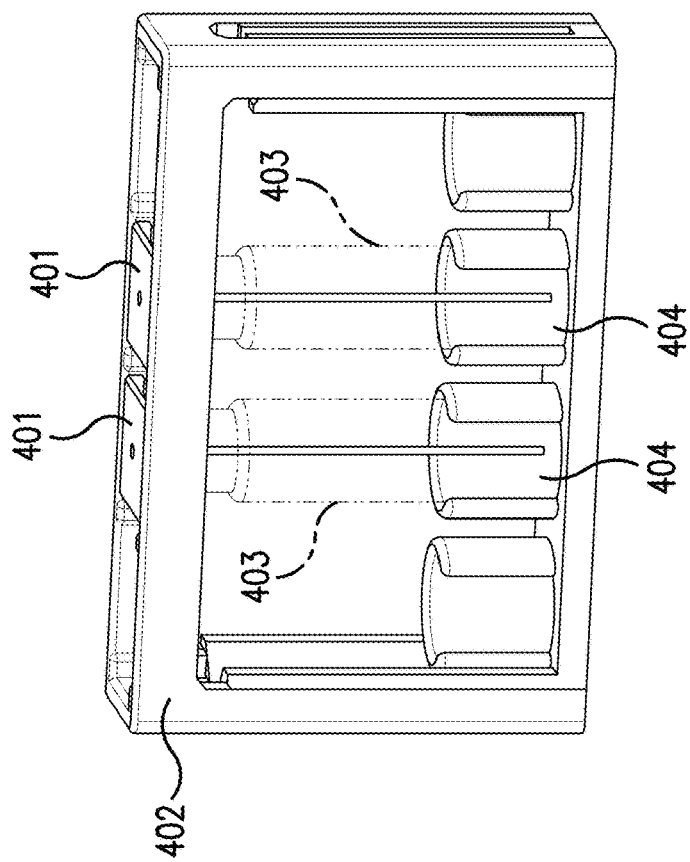
FIG. 4A is an exemplary schematic of a dipping system in accordance with certain non-limiting embodiments of the disclosed subject matter.

In certain embodiments, the disclosed system includes at least one reservoir 403 (FIGS. 4A and 4B). The reservoir 403 can be a glass jar, a plastic jar, metal jar, or combinations thereof. The reservoir 403 can include a microsphere particle, a nanoparticle particle, a polymer solution, a therapeutic agent, or combinations thereof. For example, the reservoir can include a polycaprolactone (PCL) solution. In non-limiting embodiments, the reservoir can be coupled and attached to at least one frame of the disclosed system. For example, the reservoir can be located on the frame through a jar holder 404 (FIGS. 4A and 4B). The jar holder 404 can be configured to receive at least one reservoir, and the reservoir can press-fit into the jar holder. The frame can include at least one, at least two, at least three, at least four, at least five, at least six, at least seven, at least eight, at least nine, or at least ten jar holders. The disclosed system can include two or more reservoirs.

Figure 5A:
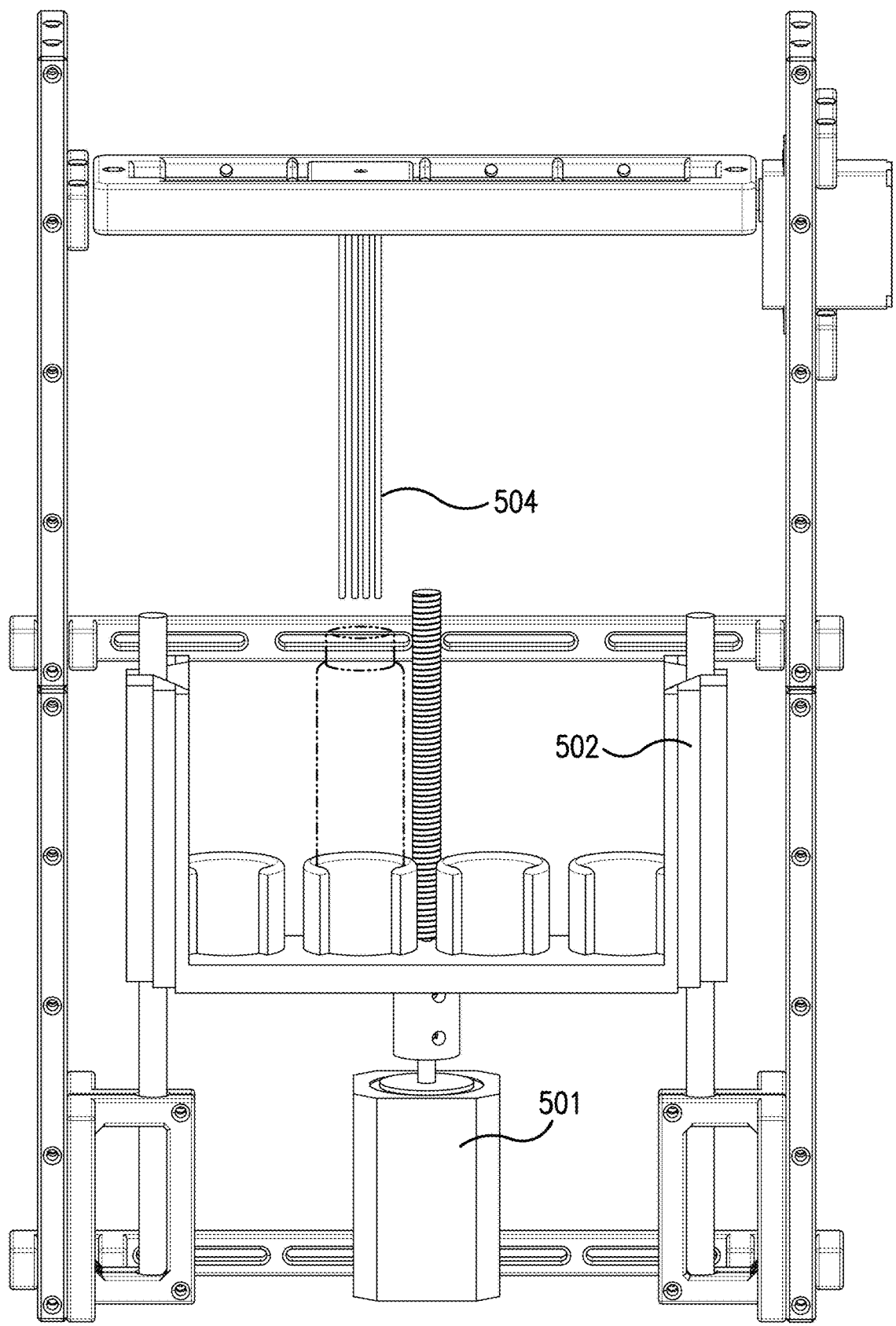
FIG. 5A is an exemplary schematic of the disclosed system with the assembled dipping system in accordance with certain non-limiting embodiments of the disclosed subject matter.
Figure 5B:
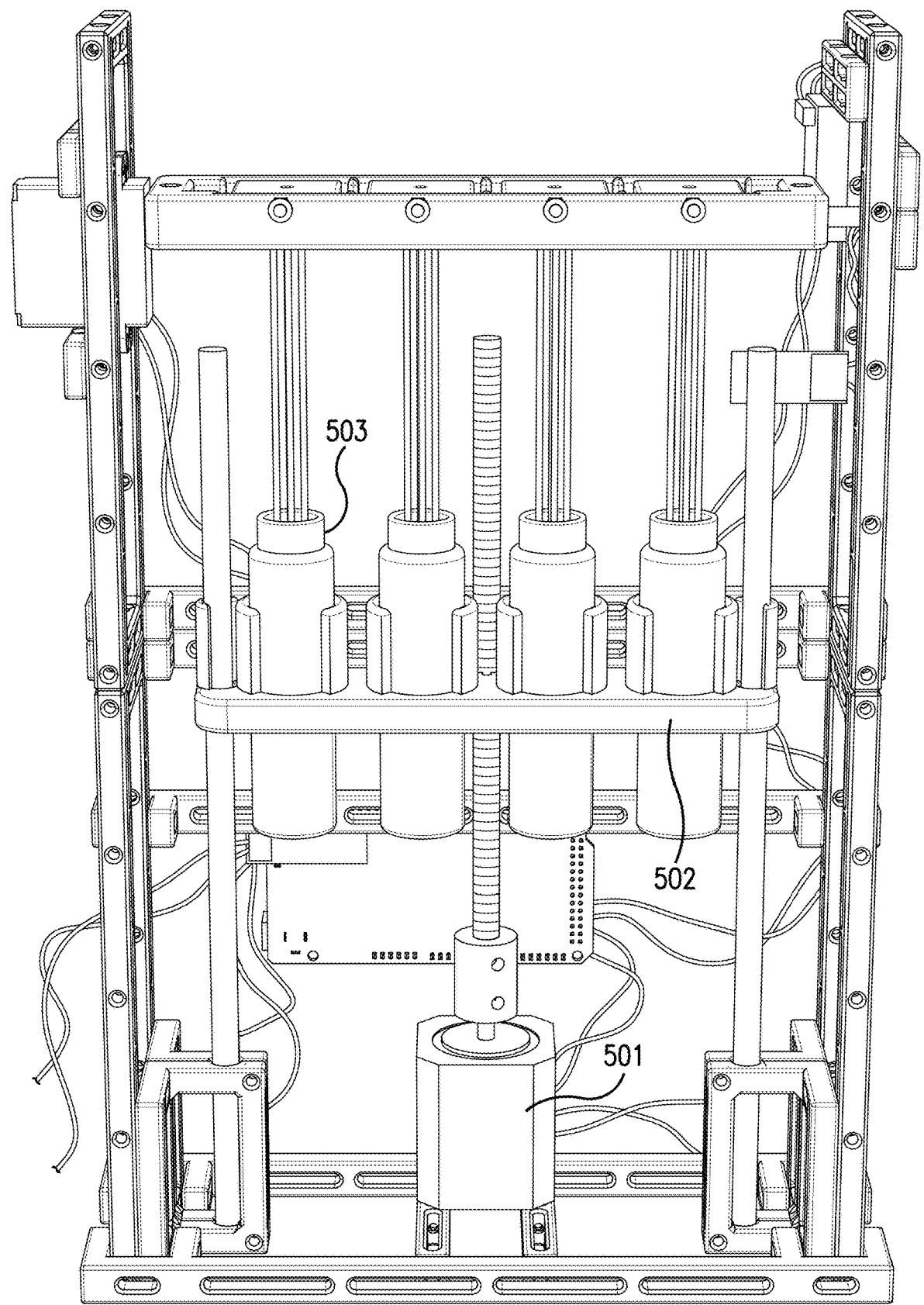
FIG. 5B is an exemplary photograph of the disclosed system with the assembled dipping system in accordance with certain non-limiting embodiments of the disclosed subject matter.
Figure 6A:
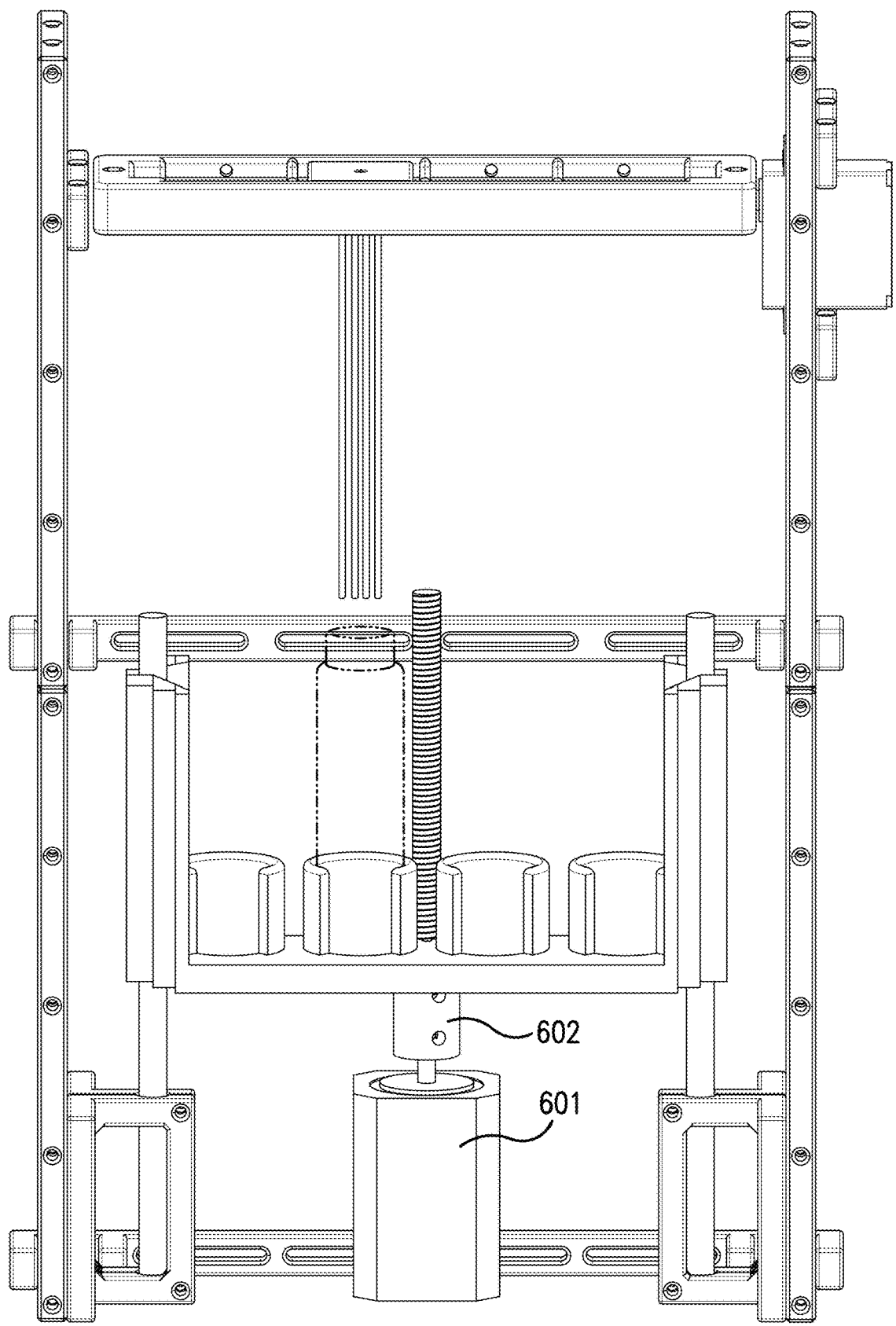
FIG. 6A is an exemplary schematic of the disclosed system at the position where a mandrel is outside of a container in accordance with certain non-limiting embodiments of the disclosed subject matter.
Figure 6B:
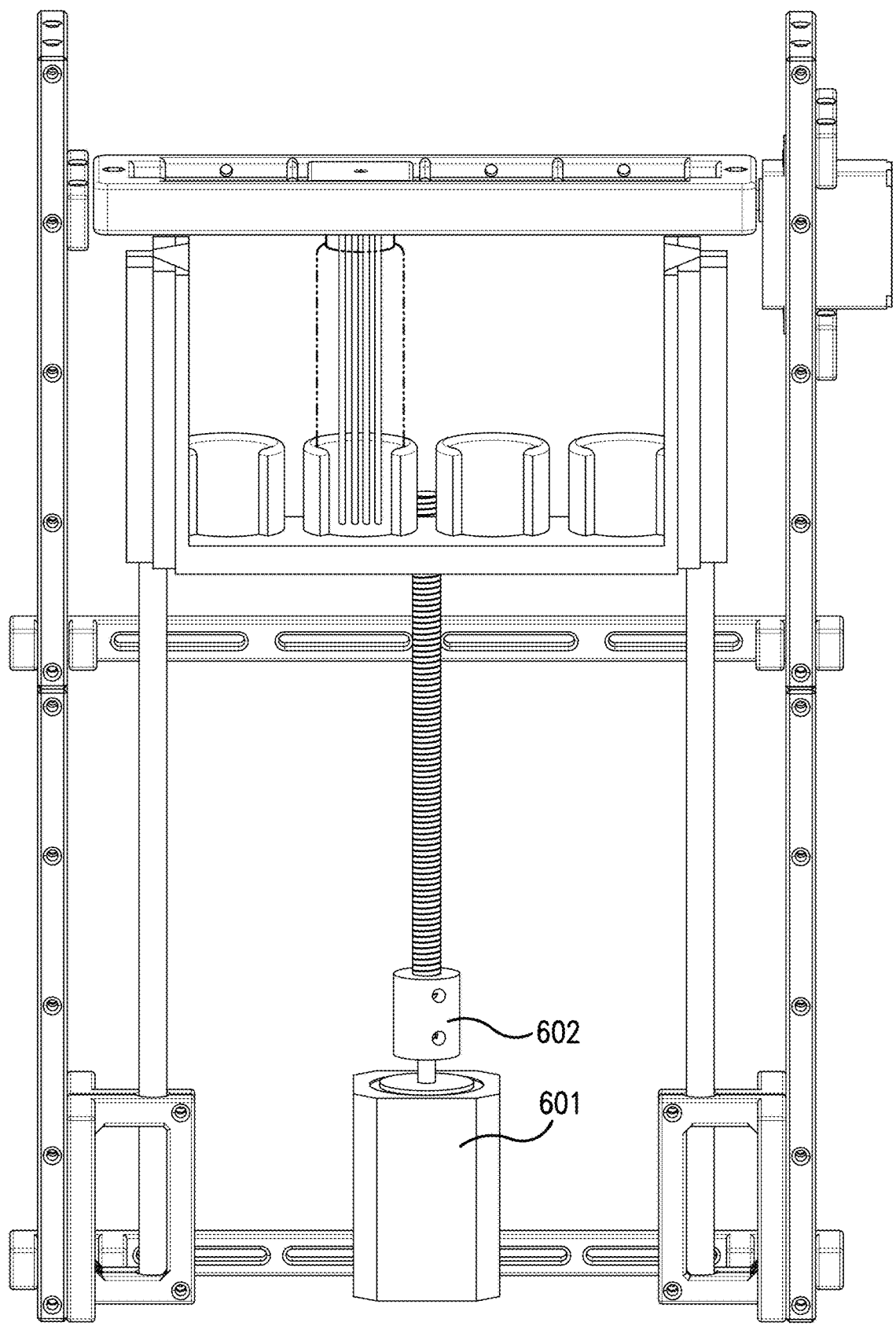
FIG. 6B is an exemplary schematic of the disclosed system at the position where a mandrel is inside of a container in accordance with certain non-limiting embodiments of the disclosed subject matter.

In certain embodiments, as shown in FIGS. 5A and 5B, the disclosed system includes a first mechanism 501, which can control a movement of at least one frame 502 of the disclosed system. The first mechanism 501 can be a motor, a cylinder, a generator, a transformer, a turbine, a piston, or combinations thereof. For example, the first mechanism can be a stepper motor. The first mechanism 501 can be coupled or attached to at least one frame and move frames of the disclosed system along a first axis (e.g., vertical axis). The first mechanism can move mandrels on each mandrel base from a first position 503 at least in part within the reservoir to a second position 504 outside the reservoir, or vice versa, by moving the mandrel holder and/or the jar holder. For example, the mandrels on each mandrel base can be mounted onto the mandrel base holder and dipped into the reservoir, which can contain a microsphere particle, a nanoparticle particle, a polymer solution (e.g., PCL), a therapeutic agent, or combinations thereof. The dipping process can be guided by the frames (e.g., mandrel base holder and jar holder) of the disclosed system. Movements of the frames (e.g., mandrel base holder and jar holder) can be manually, semi-automatically, or automatically controlled by the first mechanism. For example, as shown in FIGS. 6A and 6B, the first mechanism (e.g., a stepper motor) 601 can drive a lead screw such that the jar holder moves upward (FIG. 6B) and downward (FIG. 6A) about the vertical axis. The first mechanism (e.g., stepper motor) 601 can drive an appropriate distance by integrating a feedback loop using an end-stop 602. In certain embodiments, a lead screw, lead screws, guideposts, or combinations thereof can be oriented such that a mechanism can move upward and downward about an axis. These features can define and guide a fixed pathway of motion for a moving mechanism. In non-limiting embodiments, these pathways can be further defined using mechanical or non-mechanical (e.g., magnetically-sensitive) end-stops. For example, the movement pathway upward or downward of the jar holder can have a maximum or minimum height defined by one end-stop, two end-stops, or a series of end-stops that can define the location of a mechanism about the lead screw. Once the mandrels are dipped, then the first mechanism can subsequently lower the jar holder.

In certain embodiments, the disclosed system includes a second mechanism 701, which can control the movement of the mandrel 702, mandrel base 703, and/or mandrel holder 704 (FIG. 7A and FIG. 7B). The second mechanism 701 can be a motor, a cylinder, a generator, a transformer, a turbine, a piston, or combinations thereof. For example, the second mechanism 701 can be a stepper motor. The second mechanism can be coupled or attached to at least one frame and move frames of the disclosed system along a second axis (e.g., horizontal axis). In non-limiting embodiments, the second mechanism can rotate the mandrel 702, mandrel base 703, mandrel base holder 704, or combinations thereof along with a horizontal axis from a first orientation to second orientation. For example, mandrel bases with at least one mandrel can be mounted on the mandrel base holder. The second mechanism (e.g., stepper motor) can rotate the mandrel holder circularly. In non-limiting embodiments, the disclosed system can include a rotary encoder that can provide the location (between 0 and 360 degrees) of the mandrel base, forming a feedback loop to drive the stepper motor to orient the mandrels downward.

In certain embodiments, the first and second mechanisms can repeatedly control more than one frame of the disclosed system. For example, the nerve guide process can be dipped at least six dips in a PLC solution, which can be contained in the solution jar. Each dip can be followed with about 5 minutes of drying time, while also being placed under constant inversion. The first mechanism can drive a lead screw such that the jar holder can move upward and downward about the vertical axis. An integrated feedback loop using an end-stop can ensure that the stepper motor drives the appropriate distance. Once the mandrel is dipped and subsequently lowered, the horizontal-axis stepper motor can rotate the mandrel base holder circularly for about five minutes drying the PCL. Then, the rotary encoder can provide the location (between 0 and 360 degrees) of the mandrel base, forming a feedback loop to drive the stepper motor to orient the mandrels downward. In non-limiting embodiments, the mechanisms can control the movement of the at least one mandrel bases together or independently. The first and second mechanisms can be controlled by the disclosed microcontroller.

In certain embodiments, the disclosed system includes at least one container 705, which can receive the disclosed at least one mandrel in the second orientation (FIGS. 7A and 7B). The container 705 can comprise glass, metal, plastic, or combinations thereof. For example, the container 705 can include ABS. The container 705 can be attached or coupled to at least one frame of the disclosed system. In non-limiting embodiments, the container can include a microsphere particle, a nanoparticle particle, a polymer solution, a therapeutic agent, or combinations thereof. In certain embodiments, the disclosed system can include a third mechanism 706, which can control the movement of at least one container 705. For example, the third mechanism 706 can move at least one container from a first position away from the mandrel in the second orientation to a second position to receive the mandrel in the second orientation, or vice versa.

In some embodiments, the disclosed system can include an additional container 801, which is adapted to receive at least one mandrel. For example, after the PCL dip, the mandrel can be oriented to 90 degrees (FIGS. 7A and 7B). Afterward, the third mechanism can raise the first container containing microspheres meeting the mandrel at the 90-degree position and embedding microspheres into the PCL guide (FIGS. 7A and 7B). The mandrel is then rotated 180 degrees to be oriented at the 270-degrees position (FIGS. 8A and 8B). The third mechanism or an additional mechanism can raise the second microsphere-containing container, again meeting the mandrel and embedding microspheres into the PCL guide, this time on the opposing side (FIGS. 8A and 8B). The mandrel then can be oriented back to the 0-degree position, and the remaining dips can be performed.

In certain embodiments, the disclosed particles can include a microsphere, nanospheres, or a combination thereof. In non-limiting embodiments, the disclosed particles can comprise a double-walled particle. For example, the double-walled particles can include an active agent, wherein a poly(lactic-co-glycolic acid) layer forms a core, and a poly(lactide) layer forms a shell of the double-walled microsphere. The double-walled particles can provide sustained release of the active agent over at least seven days. The selection of the active agent can be made based on the function of the construct, and the physiological needs of the subject to be treated. For example, and not by way of limitation, active agents that can be incorporated into double-walled microspheres include chemotherapeutic drugs or agents (e.g., doxorubicin and/or cisplatin), immunosuppressive drugs or agents (e.g., tacrolimus), anti-inflammatory drugs or agents (e.g., nonsteroidal anti-inflammatory drugs), insulin, dexamethasone, growth factors (e.g., bone morphogenic protein-2, the transforming growth factor R superfamily of proteins, and/or fibroblast growth factors 1 and 2), antihyperglycemic drugs (e.g., pioglitazone), kinase inhibitors, proteins specific to neural regeneration (e.g., glial cell line-derived neurotrophic factor (GDNF), nerve growth factor (NGF), and/or brain-derived growth factor (BDGF)), or combinations thereof.

In certain embodiments, the disclosed system can include a housing. The system can be located in the housing which can monitor and/or regulate temperature and humidity within the housing.

In certain embodiments, the disclosed system can be a manual, a semi-automated, or a fully automated system. The disclosed microcontroller can control the disclosed mechanisms. The disclosed mechanisms can control the movement of the frames of the disclosed system either together or independently (FIG. 9).

One embodiment of the presently disclosed subject matter provides a system for making a construct comprising at least one frame, at least one reservoir filled with a PCL solution, at least one mandrel base adapted to be coupled to the at least one frame, a mandrel, a first mechanism configured to move the at least one mandrel base and/or the at least one reservoir along a first axis, a second mechanism configured to rotate the least one mandrel base along a second axis a first orientation to a second orientation, a container configured to receive the mandrel in the second orientation and includes a particle, and a third mechanism configured to move the container from a first position away from the mandrel in the second orientation to a second position to receive the mandrel in the second orientation. The disclosed system can also include a microcontroller which can communicate with a PCB and control movements of the frames. The PCB electronically integrates all components of the disclosed system. The mandrel can comprise glass, metal, a bioactive component, or combinations thereof. The container can include a microsphere particle, a nanoparticle particle, a polymer solution, a therapeutic agent, or combinations thereof. In certain embodiments, the frames, the mandrel base, and the container can comprise glass, metal, plastic, or combinations thereof. For example, the frames, the mandrel base, and the container can comprise ABS. The disclosed system can be located in a housing that can monitor and/or control temperature and humidity within the housing.

6.3 Methods of Making a Construct

The presently disclosed subject matter also relates to methods for making a construct. In certain embodiments, the disclosed method for making a construct includes dipping a mandrel in a first polymer solution 1001, removing the coated mandrel from the first polymer solution 1002, rotating the coated mandrel to a second orientation perpendicular or substantially perpendicular to the first orientation 1003, contacting the coated mandrel with particles to produce a particle embedded mandrel 1004, rotating the particle embedded mandrel to, or substantially to the first orientation 1005, dipping the particle embedded mandrel in a second polymer solution to deposit a second polymer layer over the particles 1006, and removing the particle embedded mandrel with the second polymer layer from the second polymer solution 1007 (FIG. 10). In non-limiting embodiments, the disclosed methods can be performed with/without the disclosed systems.

In certain embodiments, the disclosed method comprises dipping a mandrel in a first polymer solution to produce a coated mandrel, wherein the mandrel is in a first orientation. The construct can be prepared by coating at least one mandrel in a vertical orientation with a polymer solution. The disclosed mandrels can include glass, metal, a biologically-derived structure, a bioactive structure, a biodegradable structure, or combinations thereof. The polymer solution can include a PCL solution. For example, glass mandrels can be coated with a PCL solution by dipping the glass mandrels in the PCL solution and removing it from the PCL solution. In non-limiting embodiments, mandrels can be coated by the disclosed system. For example, at least one mandrels can press-fit into the disclosed mandrel base. Then, the mandrel base can be mounted onto the frames 1101 of the disclosed system, wherein the attached mandrels are in the first orientation (e.g., vertical orientation). The PCL solution can be contained in the disclosed reservoir 1102, which can be mounted onto the frames 1103 (e.g., jar holder) of the disclosed system (FIG. 11A). The disclosed microcontroller can dip the mandrels into the PCL solution in the reservoir by controlling the movement of the frames with the disclosed mechanisms (FIG. 11B). For example, the disclosed first mechanism 1104 can drive a lead screw such that the jar holder can move upward and downward along the vertical axis (FIGS. 11B and 11C).

In certain embodiments, the disclosed method comprises removing the coated mandrel from the first polymer solution and rotating the coated mandrel to a second orientation perpendicular or substantially perpendicular to the first orientation. For example, the coated mandrel can be removed from the polymer solution and rotated to a second orientation (e.g., horizontal orientation) perpendicular or substantially perpendicular to the first orientation (e.g., vertical orientation). In non-limiting embodiments, the coated mandrel can be removed from the polymer solution and rotated by the disclosed system. For example, the disclosed system can control movements of the mandrel 1105, mandrel base 1106, and/or mandrel holder 1107 using the second mechanism 1108. The second mechanism 1108 can rotate the mandrel 1105, mandrel base 1106, mandrel base holder 1107, or combinations thereof along with a horizontal axis from the first orientation to the second orientation (FIG. 11D). Once the mandrel is dipped and removed from the reservoir, the second mechanism can rotate the mandrel base holder circularly for about five minutes drying the PCL. Then, the second mechanism can stop the mandrel at the second orientation perpendicular or substantially perpendicular to the first orientation.

In certain embodiments, the disclosed method includes contacting the coated mandrel with a particle to produce a particle-embedded mandrel, wherein the particle-embedded mandrel comprises a first polymer layer, which includes at least a portion of the particle. For example, at least one particle can be embedded into the coating layer of the mandrels by contacting the particles with the coated mandrel. Any technique can be used to apply the particles to the layer of the construct so long as the process does not dissolve, denature, or otherwise negatively impact the microspheres. For example, the semi-dried and dip-coated mandrel can be contacted to the particles that are evenly spread in a container and allowed to dry. In non-limiting embodiments, the particles can be embedded using the disclosed system. For example, the disclosed system includes at least one container which can be configured to receive the mandrel in the second orientation. The particles can be contained in the container and even spread across the non-reactive surface of the container. In some embodiments, the container can include a microsphere particle, a nanoparticle particle, a double-walled particle, a polymer solution, a therapeutic agent, or combinations thereof. In non-limiting embodiments, the disclosed system can include a third mechanism that can move the container from a first position away from the mandrel in the second orientation to a second position to receive the mandrel in the second orientation or vice versa. For example, after the PCL dip, the mandrel can be oriented to 90 degrees. Afterward, the third mechanism can raise the first container containing microspheres meeting the mandrel at the 90-degree position and embedding microspheres into the mandrel (FIG. 11D). The mandrel then can be rotated 180 degrees to be oriented at the 270-degrees position (FIG. 11E). The third mechanism or an additional mechanism can raise the second microsphere-containing container, again meeting the mandrel and embedding microspheres on the opposing side of the mandrel. The polymer layer (e.g., first layer) of the particle embedded mandrel can include at least a portion of particles. In non-limiting embodiments, the coated mandrel can be dipped and removed from an additional polymer solution before contacting with the particle to produce a construct having a particle more distant from the center.

In certain embodiments, the disclosed method further includes rotating the particle embedded mandrel to, or substantially to the first orientation. For example, the mandrel then can be oriented back to the first orientation (e.g., 0-degree position) for additional dipping into a polymer solution (FIG. 11F).

In certain embodiments, the disclosed method further includes dipping the particle embedded mandrel in a first or second polymer solution to deposit a second polymer layer over the particle and removing the particle embedded mandrel with the second polymer layer from the first or second polymer solution. For example, the particle embedded mandrel can be dipped into a second polymer solution (e.g., PCL) and removed from the solution to deposit a new polymer layer (i.e., second polymer layer). See FIGS. 11G and 11H. The disclosed methods can be repeated until the pre-determined thickness or number of coating layers is achieved. For example, the additional dipping and removing steps can also be performed using the disclosed system similar to the previous dipping and removing steps. In non-limiting embodiments, the disclosed system can repeat dipping and removing steps between about six and about ten times to produce a predetermined wall thickness after a lumen is created upon removing the mandrel. The predetermined wall thickness can be about 10 microns, about 50 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, about 1000 microns, about 2000 microns, or about 3000 microns.

6.4 Construct

One embodiment of the presently disclosed subject matter provides an implantable construct prepared by the systems and methods set forth above. The implantable construct can locally deliver an active agent (e.g., bioactive neurotrophic factor) in physiologically relevant or supraphysiologic concentrations for pre-selected periods (e.g., for at least 50 days). The presently disclosed subject matter is equally applicable to any medical device for which it is desired to deliver an active agent over an extended period of time. The presently disclosed subject matter can be used in a human, non-human primate, non-human mammal, rodent, or other non-human animal subjects (FIG. 12A).

In certain embodiments, the construct can comprise a biodegradable polymer tube which has a lumen (FIG. 12B). In non-limiting embodiments, the lumen can comprise an inner 1201 layer and an outer layer 1202. The inner layer can include a biodegradable polymer, into which are embedded the disclosed particles, an active agent, or a combination thereof. The outer layer can comprise a biodegradable polymer without particles or an active agent, wherein said outer layer encapsulates the inner layer. In certain embodiments, the outer layer can comprise a biodegradable polymer with the disclosed particles or the active agent, and the inner layer can comprise a biodegradable polymer without particles or an active agent. In some embodiments, the outer and inner layers can include a biodegradable polymer with the disclosed particles or the active agent. In non-limiting embodiments, the outer and inner layers can include a biodegradable polymer without particles.

In certain embodiments, the disclosed particles can include a microsphere, a nanosphere, or a combination thereof. In non-limiting embodiments, the disclosed particles can comprise double-walled microspheres. The double-walled microspheres can include an active agent. The selection of the active agent can be made based on the function of the medical device and the physiological needs of the subject to be treated. For example, and not by way of limitation, other agents that can be incorporated into double-walled microspheres include chemotherapeutic drugs or agents (e.g., doxorubicin and/or cisplatin), immunosuppressive drugs or agents (e.g., tacrolimus), anti-inflammatory drugs or agents (e.g., nonsteroidal anti-inflammatory drugs), insulin, dexamethasone, growth factors (e.g., bone morphogenic protein-2, the transforming growth factor R superfamily of proteins, and/or fibroblast growth factors 1 and 2), antihyperglycemic drugs (e.g., pioglitazone), kinase inhibitors, proteins specific to neural regeneration (e.g., glial cell line-derived neurotrophic factor (GDNF), nerve growth factor (NGF), and/or brain-derived growth factor (BDGF)), or combinations thereof.

In non-limiting embodiments, the disclosed double-walled microspheres can comprise an inner wall and outer wall. For example, a poly(lactide) wall can be the inner wall, and the poly(lactic-co-glycolic acid) wall can be an outer wall. Alternatively, the poly(lactide) wall can be the outer wall, and the poly(lactic-co-glycolic acid) wall can be an inner wall. The poly(lactic-co-glycolic acid) layer forms a core, and the poly(lactide) layer forms a shell of the double-walled microsphere, and the microspheres provide sustained release of the active agent over pre-determined periods. The active agent can be released from double-walled microspheres over at least 1 day, at least 3 days, at least 7 days, at least 14 days, at least 30 days, at least 50 days, at least 80 days, or at least 100 days.

In certain embodiments, the disclosed construct can be used as a nerve guide. The disclosed construct can allow transected peripheral nerves to cross from a proximal to a distal nerve stump. Delivery of an active agent (e.g., neurotrophic factors) can enhance regeneration and repair nerves across large defects. Glial Cell Line-Derived Neurotrophic Factor (GDNF) can be the active agent and released from the disclosed construct. The disclosed construct can promote Schwann cell proliferation and migration. Other nerve factors that can be comprised in the microspheres include, but are not limited to, glial growth factor 2 (GGF2), brain-derived neurotrophic factor (BDNF), novel neurotrophin-1 (NNT1), Ciliary neurotrophic factor (CNTF), nerve growth factor (NGF), and neurotrophin-3 (NT-3). These agents, or a combination thereof, can be provided in addition to, or in place of, GDNF.

6.5 Methods of Promoting Tissue Regeneration

One embodiment of the presently disclosed subject matter provides a method of promoting tissue regeneration using the implantable construct prepared by the systems and methods set forth above. The method can include introducing a construct as described above into an area of injury or disease of a subject. The injury and disease can be caused, for example, by accidental or surgical trauma, infarction, infection, and/or inflammation.

In certain embodiments, the disclosed techniques can be used for treating an injured tissue, wherein a proximal and a distal end of the injured tissue are separated by a gap. In certain non-limiting embodiments, the composite nerve guide can be introduced into an area of the injury to covers at least about 50 percent, or at least about 75 percent, or at least about 80 percent, or at least about 90 percent, of the gap between the proximal and distal nerve ends. In certain non-limiting embodiments, the gap is at least about 1 cm, at least about 2 cm, at least about 3 cm, at least about 4 cm, or at least about 5 cm. In certain non-limiting embodiments, the gap is up to about 3 cm, about 4 cm, about 5 cm, about 6 cm, about 7 cm, about 8 cm, about 9 cm, or about 10 cm.

In certain embodiments, the disclosed method can be used for treating any type of tissue. In non-limiting embodiments, the disclosed construct can be introduced to treat the injury of epithelial, connective, muscular, nervous, or combinations thereof. For example, and not by way of limitation, a target tissue can be a nerve of the central nervous system, a nerve of the peripheral nervous system, a bone, a skin, or combinations thereof.

All patents, patent applications, publications, product descriptions, and protocols, cited in this specification are hereby incorporated by reference in their entireties. In case of a conflict in terminology, the present disclosure controls.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

What is claimed is:

1. A system for making a construct comprising:
at least one frame;
a reservoir coupled to the at least one frame;
a mandrel base coupled to the at least one frame;
a mandrel coupled to the mandrel base, wherein the mandrel is selected from the group consisting of a biodegradable structure, a biologically-derived structure, a bioactive structure, and combinations thereof;
a first mechanism configured to be coupled to the at least one frame and configured to move the at least one frame along a first axis;
a second mechanism configured to be coupled to the at least one frame and configured to rotate the least one mandrel base along a second axis between a first orientation and a second orientation; and
a container configured to be coupled to the at least one frame and configured to receive the mandrel in the second orientation.

2. The system of claim 1, wherein the construct comprises a tube having a lumen.

3. The system of claim 2, wherein the tube comprises an inner layer and an outer layer, wherein the inner layer is selected from the group consisting of a first biodegradable polymer, a particle, an active agent, and combinations thereof, wherein the outer layer is selected from the group consisting of a second biodegradable polymer, the particle, the active and combinations thereof.

4. The system of claim 3, wherein the particle is selected from the group consisting of a microsphere, a nanosphere, and a combination thereof.

5. The system of claim 3, wherein the particle comprises a double-walled particle, wherein the double-walled particle comprises the active agent that is released over a predetermined period of time.

6. The system of claim 1, wherein the mandrel comprises a cylindrical structure of purified collagen or a decellularized scaffold.

7. The system of claim 1, wherein the first axis is a vertical axis, and the first mechanism changes a location of the mandrel from a first position at least in part within the reservoir to a second position outside the reservoir, or vice versa.

8. The system of claim 1, wherein the second axis is a horizontal axis, wherein the first orientation is a vertical orientation, wherein the second orientation is a horizontal orientation.

9. The system of claim 1, wherein the container includes a particle, wherein the particle is selected from the group consisting of a microsphere, a nanosphere, and a combination thereof.

10. The system of claim 8, further comprising a third mechanism configured to move the container from a first position away from the mandrel in the second orientation to a second position to receive the mandrel in the second orientation.

11. The system of claim 1, wherein the reservoir comprises a polymer solution, optionally, wherein the polymer solution is a polycaprolactone (PCL) solution.

12. The system of claim 1, further comprising a housing configured to monitor and regulate temperature and humidity within the housing, wherein the system is located in the housing.

13. The system of claim 1, further comprising a microcontroller, wherein the first and second mechanisms are manually, semi-automatically, or automatically controlled by the microcontroller, wherein the microcontroller monitors, records, and saves data related to conditions of the disclosed system, wherein the conditions include the temperature and the humidity.

14. The system of claim 1, wherein the system comprises two or more mandrel bases and reservoirs, wherein the first and second mechanisms control movement of the two or more mandrel bases together or independently.

* * * * *